United States Patent
Takayama

(10) Patent No.: US 12,102,404 B2
(45) Date of Patent: Oct. 1, 2024

(54) BENDING MECHANISM AND MEDICAL MANIPULATOR

(71) Applicant: OLYMPUS CORPORATION, Hachioji (JP)

(72) Inventor: Hiroyuki Takayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1199 days.

(21) Appl. No.: 16/854,087

(22) Filed: Apr. 21, 2020

(65) Prior Publication Data
US 2020/0246098 A1 Aug. 6, 2020

Related U.S. Application Data

(63) Continuation of application No. PCT/JP2017/039661, filed on Nov. 2, 2017.

(51) Int. Cl.
*A61B 34/00* (2016.01)
*B25J 1/02* (2006.01)
*B25J 9/10* (2006.01)

(52) U.S. Cl.
CPC ............. *A61B 34/71* (2016.02); *A61B 34/70* (2016.02); *B25J 1/02* (2013.01); *B25J 9/10* (2013.01)

(58) Field of Classification Search
None
See application file for complete search history.

(56) References Cited

U.S. PATENT DOCUMENTS

| | | | | |
|---|---|---|---|---|
| 3,659,329 | A | * | 5/1972 | Walker .................. H02K 15/10 29/283 |
| 6,699,235 | B2 | | 3/2004 | Wallace et al. |
| 7,121,781 | B2 | | 10/2006 | Sanchez |
| 2003/0018323 | A1 | | 1/2003 | Wallace et al. |
| 2004/0253079 | A1 | | 12/2004 | Sanchez |
| 2007/0078456 | A1 | | 4/2007 | Dumbauld et al. |
| 2007/0106297 | A1 | | 5/2007 | Dumbauld et al. |
| 2008/0195144 | A1 | | 8/2008 | Hashimoto |

(Continued)

FOREIGN PATENT DOCUMENTS

| | | | |
|---|---|---|---|
| AU | 2007/231795 A1 | | 5/2008 |
| CA | 2609492 A1 | | 5/2008 |

(Continued)

OTHER PUBLICATIONS

Aug. 17, 2021 Office Action issued in U.S. Appl. No. 16/680,715.

(Continued)

*Primary Examiner* — Sana Sahand
(74) *Attorney, Agent, or Firm* — Oliff PLC

(57) ABSTRACT

A bending mechanism includes: an elongated support member; a swivel that is pivotably connected to a distal end of the support member; a first link that can transmit a driving force applied at the proximal end, to make the swivel pivot with respect to the support member; a second link that can transmit a driving force applied at the proximal end, to make the swivel pivot with respect to the support member; and a connector that is provided on at least one of the first and second links and that can switch the coupled state of one of the first and second links when a pivoting angle of the swivel exceeds a threshold such that the permissible stress of the one of the links has become less than the permissible stress of the other.

11 Claims, 19 Drawing Sheets

(56) References Cited

U.S. PATENT DOCUMENTS

| | | |
|---|---|---|
| 2010/0204697 A1 | 8/2010 | Dumbauld et al. |
| 2011/0196419 A1 | 8/2011 | Cooper |
| 2012/0123441 A1 | 5/2012 | Au et al. |
| 2012/0221146 A1 | 8/2012 | Zhang et al. |
| 2013/0319143 A1 | 12/2013 | Huang et al. |
| 2014/0194873 A1 | 7/2014 | Dumbauld et al. |
| 2015/0141756 A1 | 5/2015 | Cheng et al. |
| 2015/0289942 A1 | 10/2015 | Au et al. |
| 2016/0038239 A1 | 2/2016 | Yamanaka et al. |
| 2016/0135914 A1* | 5/2016 | Isoda ................. A61B 34/71 606/130 |
| 2016/0256183 A1 | 9/2016 | Cooper |
| 2016/0310221 A1 | 10/2016 | Bar et al. |
| 2017/0080581 A1 | 3/2017 | Iida et al. |
| 2017/0304014 A1 | 10/2017 | Au et al. |
| 2019/0183592 A1 | 6/2019 | Shelton, IV et al. |
| 2019/0269473 A1 | 9/2019 | Takayama et al. |
| 2020/0078122 A1 | 3/2020 | Takayama |
| 2020/0121343 A1 | 4/2020 | Cooper |
| 2020/0146761 A1 | 5/2020 | Au et al. |
| 2020/0297438 A1 | 9/2020 | Shelton, IV et al. |

FOREIGN PATENT DOCUMENTS

| | | |
|---|---|---|
| EP | 1913879 A1 | 4/2008 |
| EP | 2105105 A1 | 9/2009 |
| EP | 3025669 A1 | 6/2016 |
| EP | 3159124 A1 | 4/2017 |
| JP | H06-008178 A | 1/1994 |
| JP | H06-262360 A | 9/1994 |
| JP | 2003-079638 A | 3/2003 |
| JP | 2007-044330 A | 2/2007 |
| JP | 4402313 B2 | 1/2010 |
| JP | 2012-125877 A | 7/2012 |
| JP | 2014-138879 A | 7/2014 |
| JP | 2015-023886 A | 2/2015 |
| JP | 2016-002414 A | 1/2016 |
| WO | 2011/059015 A1 | 5/2011 |
| WO | 2011/097095 A1 | 8/2011 |
| WO | 2012/064528 A1 | 5/2012 |
| WO | 2014/129362 A1 | 8/2014 |
| WO | 2015/012023 A1 | 1/2015 |
| WO | 2015/194321 A1 | 12/2015 |
| WO | 2018/100607 A1 | 6/2018 |
| WO | 2018/225212 A1 | 12/2018 |

OTHER PUBLICATIONS

Mar. 29, 2021 Office Action issued in U.S. Appl. No. 16/417,728.
Jan. 14, 2020 Office Action issued in Japanese Patent Application No. 2018-553520.
Feb. 7, 2017 International Search Report issued in PCT Application No. PCT/JP2016/085313.
Feb. 7, 2017 Written Opinion of the International Searching Authority issued in PCT Application No. PCT/JP2016/085313.
Aug. 29, 2017 International Search Report issued in PCT Application No. PCT/JP2017/021311.
Aug. 29, 2017 Written Opinion of the International Searching Authority issued in PCT Application No. PCT/JP2017/021311.
Jan. 23, 2018 International Search Report issued in PCT Application No. PCT/JP2017/039661.

* cited by examiner

FIG. 18
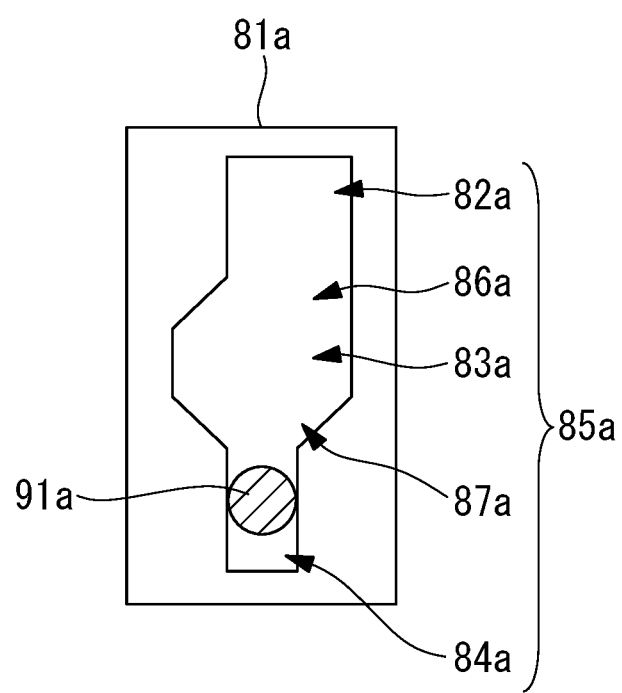
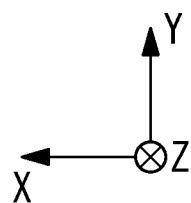

BENDING MECHANISM AND MEDICAL MANIPULATOR

CROSS-REFERENCE TO RELATED APPLICATIONS

This is a continuation of International Application PCT/JP2017/039661 which is hereby incorporated by reference herein in its entirety.

TECHNICAL FIELD

The present disclosure relates to a bending mechanism and a medical manipulator.

BACKGROUND

A medical manipulator is known to include a bending joint for changing the direction of a treatment tool provided at a distal end.

In such a medical manipulator, two links that are disposed along the insertion part and that are connected to a pivoting member located closer to the distal end than the bending joint is are pushed and pulled, thereby making the pivoting member pivot and making the treatment tool, which is fixed to the pivoting member, pivot.

SUMMARY

According to one aspect, the present disclosure relates to a bending mechanism including: an elongated support member, and a swivel that is connected to a distal end of the support member so as to be pivotable about an axis intersecting a longitudinal axis of the support member; a first link and a second link that are disposed opposite with each other along the longitudinal axis of the support member. The first and second links can transmit a driving force received at their proximal ends, to make the swivel pivot with respect to the support member. The bending mechanism also includes a handle that can be operated to make the swivel pivot with respect to the support member, by a pivoting angle determined in accordance with an operation amount. The bending mechanism further includes a connector that is provided on at least one of the first and second links, and that can switch a coupled state of one of the links when a pivoting angle of the swivel exceeds a threshold such that a permissible stress of the one link becomes less than a permissible stress of the other link. The connector includes a groove cam that has a guide groove, and an engagement part of the one link can be engaged with the guide groove of the groove cam in the longitudinal-axis direction. An engagement position in the longitudinal-axis direction between the guide groove and the engagement part can be moved in accordance with the operation amount of the handle.

BRIEF DESCRIPTION OF DRAWINGS

FIG. 18 is an enlarged sectional view of a groove cam in an exemplary embodiment.

DETAILED DESCRIPTION

A bending mechanism 5 and a medical manipulator 1 according to an exemplary embodiment will be described below with reference to the drawings.

Figure 1:
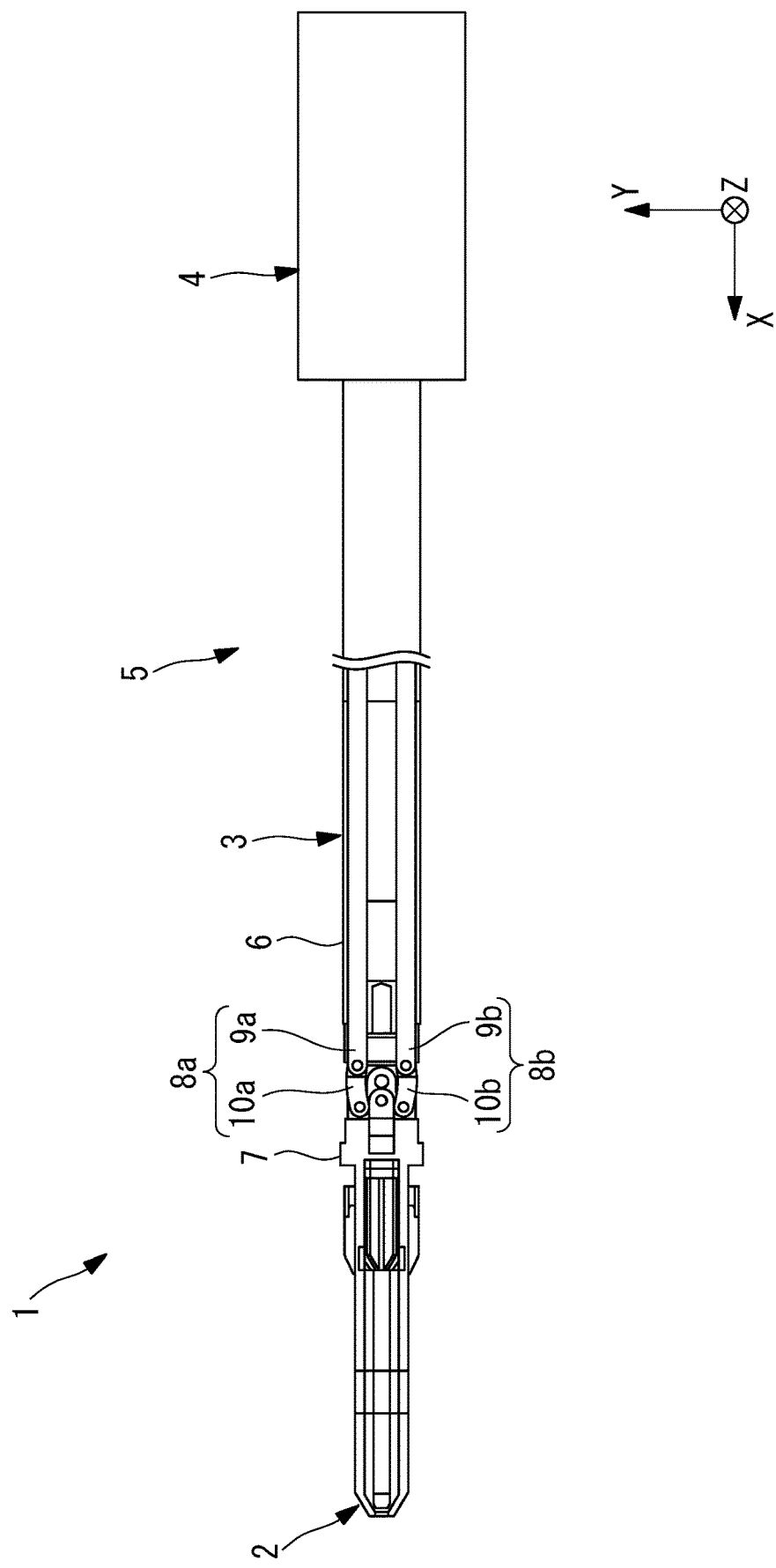
FIG. 1 is a view showing the overall configuration of a medical manipulator according to an exemplary embodiment of the present disclosure.

As shown in FIG. 1, the medical manipulator 1 of this embodiment includes a treatment tool 2 that is used to treat an affected area, an elongated insertion part 3, and an operating part (handle) 4 that is connected to a proximal end of the insertion part 3. The insertion part 3 and the operating part 4 constitute the bending mechanism 5. The treatment tool 2 is mounted at a pivoting member (swivel) 7 in the insertion part 3, to be described later.

As shown in FIG. 1, the insertion part 3 includes: an elongated support member 6; the pivoting member 7, which is supported at a distal end of the support member 6 so as to be pivotable about a pivot axis perpendicular to the longitudinal axis of the support member 6; and two pairs of links 8a and 8b that transmit a driving force applied at the operating part 4, which is located at a proximal end of the support member 6, to make the pivoting member 7 pivot with respect to the support member 6. The respective pairs of links 8a and 8b include: long first links (first driving-force transmission member, second driving-force transmission member, distal-end transmission members) 9a and 9b that are disposed along the longitudinal axis of the support member 6; and short links 10a and 10b that are coupled to the first links 9a and 9b, respectively, and to the pivoting member 7 so as to be pivotable about axes parallel to the pivot axis.

Here, coordinate axes that include the X-axis, the Y-axis, and the Z-axis shown in FIG. 1 will be defined. With the coordinate axes, the longitudinal axis of the support member 6 is defined as the X-axis, and the positive direction of the X-axis is defined as the left direction in FIG. 1, where the treatment tool 2 is provided. Furthermore, a radial direction of the support member 6 perpendicular to the X-axis is defined as the Y-axis, and the positive direction of the Y-axis is defined as the upward direction in FIG. 1.

Furthermore, the Z-axis, which is perpendicular to both the X-axis and the Y-axis, is defined, and the positive direction of the Z-axis is defined as such a direction as to penetrate FIG. 1 from the front to the back of FIG. 1. The coordinate axes, which are indicated in the subsequent figures, are correlated with one another. Note that, the X-axis positive direction is also called a distal-end direction or a distal end, and the X-axis negative direction is also called a proximal-end direction or a proximal end.

Figure 2:
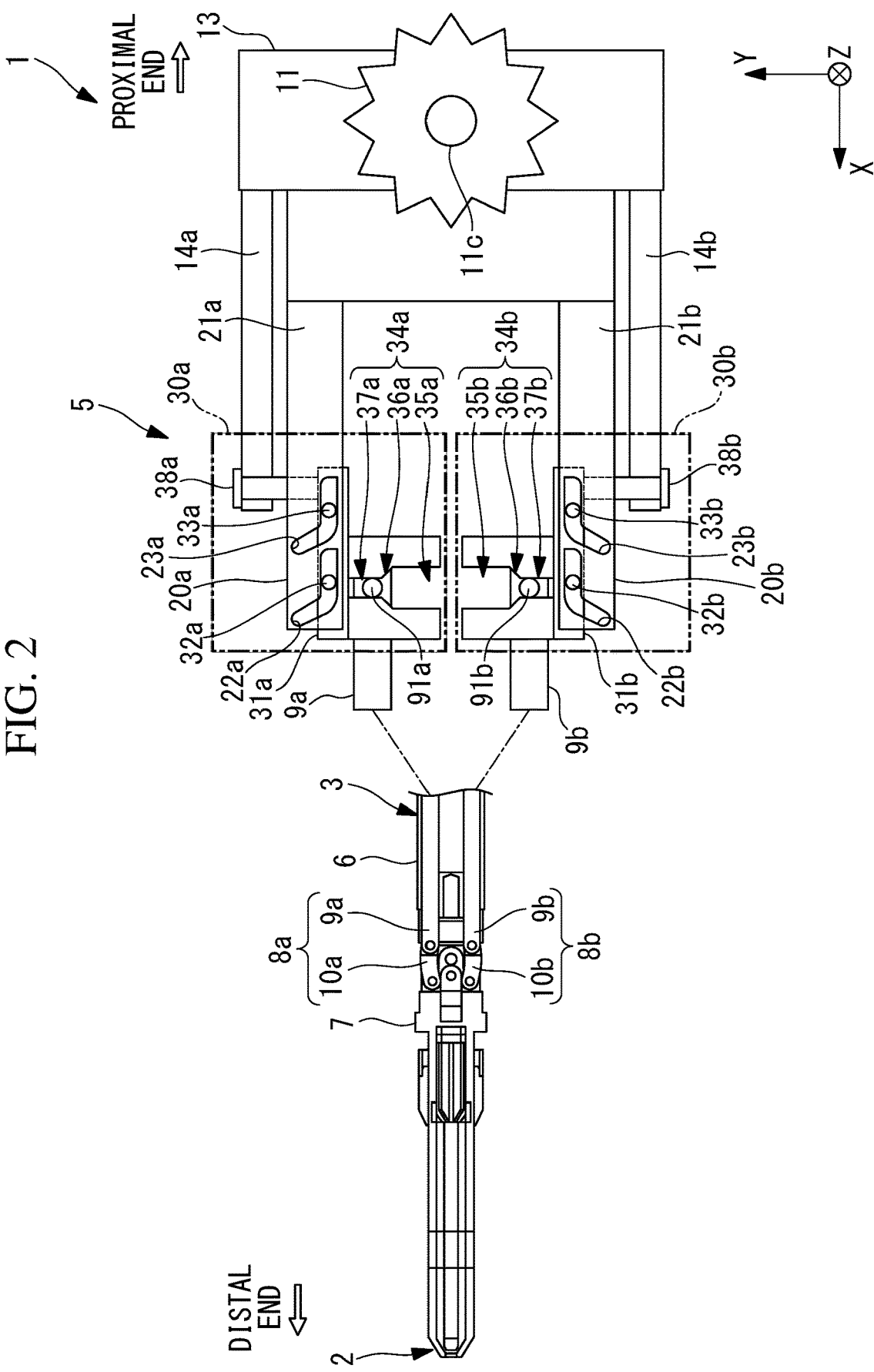
FIG. 2 is a sectional view showing a portion of the medical manipulator shown in FIG. 1, in a state in which a bending mechanism is not bent.

FIG. 2 shows the medical manipulator 1 in a state in which the pivoting member 7 does not pivot (is not bent), thus being parallel to the X-axis. As shown in FIG. 2, the operating part 4 includes: a base 13; a handle 11 to which a driving force is applied by being operated by an operator and that is rotatably mounted on the base 13; and the bending mechanism 5, which supplies the driving force applied to the handle 11 to the two pairs of links 8a and 8b and which can make the pivoting member 7 pivot.

The bending mechanism 5 includes: two second links (first driving-force transmission member, second driving-force transmission member, proximal-end transmission members) 14a and 14b that are supported on the base 13 so as to be linearly movable in the longitudinal directions of the links 8a and 8b; rack gears (not shown) that are mounted on the second links 14a and 14b; a pinion gear (not shown) that is provided on the handle 11, that is disposed between the two parallel second links 14a and 14b, and that is engaged with the rack gears; and coupling portions (connectors) 30a and 30b that change force transmission states between the first links 9a and 9b and the second links 14a and 14b. Note that the first link 9a and the second link 14a correspond to a first driving-force transmission member in the claims, and the first link 9b and the second link 14b correspond to a second driving-force transmission member in the claims.

When the handle 11 is rotated about a handle center shaft 11c, the second links 14a and 14b are linearly moved along the X-axis via the rack gears and the pinion gear. In this embodiment, when the handle 11 is rotated clockwise, the second link 14a, which is shown at the upper side in FIG. 2, is moved toward the proximal end, and the second link 14b, which is shown at the lower side in FIG. 2, is moved toward the distal end. When the handle 11 is rotated counterclockwise, the second link 14a is moved toward the distal end, and the second link 14b is moved toward the proximal end.

Because the respective coupling portions 30a and 30b are configured symmetrically about the ZX-plane that includes the central axis of the support member 6, in this embodiment, the coupling portion 30a will be described, and a description of the coupling portion 30b will be omitted. Reference signs of the coupling portion 30a and the coupling portion 30b differ only at the letters "a" and "b" appended to the reference signs, and the reference signs before the letters correspond to each other.

The coupling portion 30a includes: a fixing pin 38a whose position along the X-axis with respect to the second link 14a is fixed; a groove cam 31a whose position along the X-axis with respect to the second link 14a is fixed by the fixing pin 38a; an engagement part 91a that is formed at a proximal end of the first link 9a; and an intermediate member 21a that is fixed to the base 13 and that extends from the base 13 toward the distal end.

The fixing pin 38a penetrates the second link 14a from the outside in the radial direction and fixes the groove cam 31a from the outside in the radial direction. The fixing pin 38a can be moved within a predetermined range along the Y-axis direction. The groove cam 31a has a guide groove 34a that has, as the central axis, an axis parallel to the Y-axis; and two engagement pins 32a and 33a that protrude in the Z-axis negative direction. The guide groove 34a has, in order from the radially outer side, a small-width groove (restricting area) 37a, a tapered groove 36a, and a large-width groove (free-movement area) 35a.

The small-width groove 37a has, in the ZX-plane, a rectangular cross section having fixed lengths along the X-axis and the Z-axis. The large-width groove 35a has, in the ZX-plane, a rectangular cross section having a length, along the X-axis, longer than the small-width groove 37a and a length, along the Z-axis, equal to the small-width groove 37a. The tapered groove 36a has an inclined rectangular cross section whose cross-sectional area gradually increases along the Y-axis from the small-width groove 37a to the large-width groove 35a. The respective lengths of the small-width groove 37a, the large-width groove 35a, and the tapered groove 36a along the Y-axis are set according to the bending angle of the pivoting member 7.

The engagement pins 32a and 33a are formed on the same axis parallel to the X-axis. The engagement pins 32a and 33a have cylindrical shapes extending in the Z-axis negative direction. Two slits 22a and 23a with which the engagement pins 32a and 33a are respectively engaged are formed in the intermediate member 21a. As shown in FIG. 2, the slits 22a and 23a are curved slits in which the engagement pins 32a and 33a, which are engaged with the slits 22a and 23a, are moved toward the radially outer side as the engagement pins 32a and 33a come closer to the distal end.

As shown in FIG. 2, the engagement part 91a of the first link 9a is engaged with the guide groove 34a of the groove cam 31a. The engagement part 91a has a cylindrical shape extending from the proximal end of the first link 9a in the Z-axis negative direction. The engagement part 91a is formed such that the diameter of the cylindrical shape thereof becomes equal to the length of the small-width groove 37a of the guide groove 34a along the X-axis. In the state in which the pivoting member 7 is not bent, shown in FIG. 2, the positions of the second links 14a and 14b along the X-axis are the same. In this case, the engagement part 91a and an engagement part 91b respectively formed on the first links 9a and 9b are respectively engaged with the small-width groove 37a of the guide groove 34a and a small-width groove 37b of a guide groove 34b. In other words, the engagement positions of the engagement parts 91a and 91b with respect to the guide grooves 34a and 34b are located in a plane parallel to the YZ-plane in which the positions thereof in the small-width grooves 37a and 37b along the X-axis are regulated. Furthermore, the engagement pins 32a and 33a, which are formed on the groove cam 31a, are engaged with the slits 22a and 23a in the vicinity of the centers of the slits 22a and 23a, and engagement pins 32b and 33b that are formed on a groove cam 31b are engaged with slits 22b and 23b in the vicinity of the centers of the slits 22b and 23b. In the vicinity of the centers of the slits 22a, 23a, 22b, and 23b, the engagement pins 32a, 33a, 32b, and 33b, which are engaged therewith, are located at radially inner sides of the slits 22a, 23a, 22b, and 23b.

Figure 3:
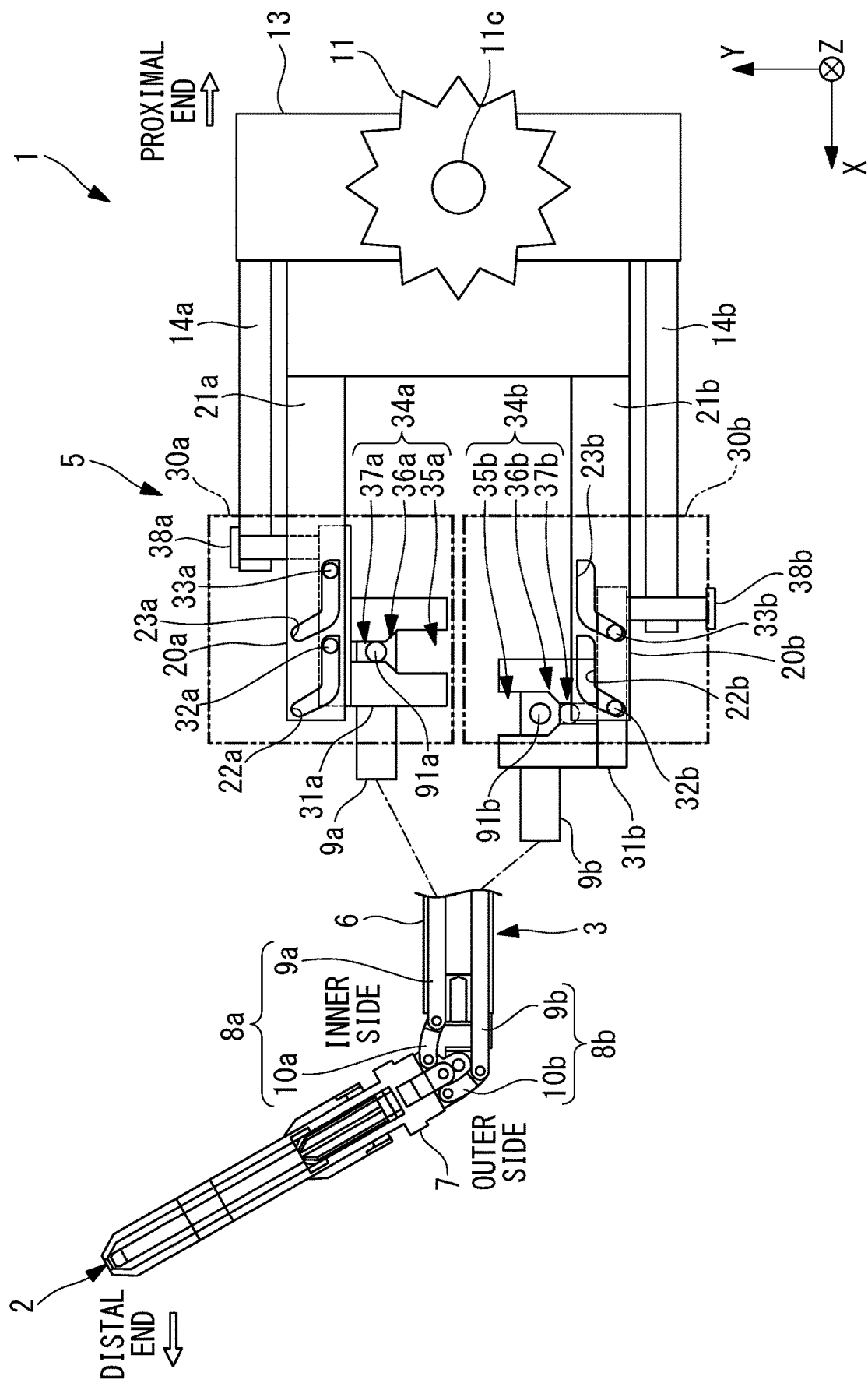
FIG. 3 is a sectional view showing the aforementioned portion of the medical manipulator shown in FIG. 1, in a state in which the bending mechanism is bent.

FIG. 3 shows the medical manipulator 1 when the handle 11 is rotated clockwise, thus bending the pivoting member 7. When the handle 11 is rotated clockwise, the second link 14a is moved toward the proximal end, and the second link 14b is moved toward the distal end. When the second link 14a is moved toward the proximal end, the fixing pin 38a, which is fixed at the distal end of the second link 14a, and the groove cam 31a, which is fixed to the fixing pin 38a, are moved toward the proximal end. As a result, the engagement pins 32a and 33a, which are formed on the groove cam 31a, are moved toward the proximal end, inside the slits 22a and 23a, with which the engagement pins 32a and 33a are engaged. Although the engagement pins 32a and 33a are moved, inside the slits 22a and 23a, in the X-axis negative direction, the engagement pins 32a and 33a are not moved along the Y-axis. Specifically, the groove cam 31a, which has the engagement pins 32a and 33a, is not moved in the Y-axis direction. As a result, the positional relationship between the guide groove 34a of the groove cam 31a and the engagement part 91a, which is engaged with the guide groove 34a, along the Y-axis does not change, so that the engagement part 91a is still engaged with the small-width groove 37a of the guide groove 34a.

When the handle 11 is rotated clockwise, and the second link 14b is moved toward the distal end, a fixing pin 38b that is fixed at a distal end of the second link 14b and the groove cam 31b, which is fixed to the fixing pin 38b, are moved toward the distal end. As a result, the engagement pins 32b and 33b, which are formed on the moved groove cam 31b, are moved toward the distal end, inside the slits 22b and 23b, with which the engagement pins 32b and 33b are engaged. The engagement pins 32b and 33b are moved toward the distal end along the shapes of the slits 22b and 23b, and, at the same time, are moved radially outward (in the Y-axis negative direction). As a result, the positional relationship between the guide groove 34b of the groove cam 31b and the engagement part 91b, which is engaged with the guide groove 34b, along the Y-axis changes, and the position of the engagement part 91b along the Y-axis changes from the small-width groove 37b to a large-width groove 35b, as shown in FIG. 3. In the state in which the position of the engagement part 91b along the Y-axis is located at the large-width groove 35b, because the diameter of the engagement part 91b is less than the length of the large-width groove 35b along the X-axis, the engagement part 91b can be moved within a predetermined range along the X-axis. In this case, the engagement position of the engagement part 91b with respect to the guide groove 34b is in a plane parallel to the YZ-plane in which the position thereof in the small-width groove 37b along the X-axis is regulated.

When the medical manipulator 1 is changed from the state shown in FIG. 3 to the state shown in FIG. 2, the handle 11 is rotated counterclockwise, thereby moving the second link 14a toward the distal end and moving the second link 14b toward the proximal end. At this time, in the coupling portion 30b, the groove cam 31b, which is fixed to the fixing pin 38b, is moved toward the proximal end. When the engagement pins 32b and 33b, which are formed on the groove cam 31b, are moved toward the proximal end and radially inward along the shapes of the slits 22b and 23b, the groove cam 31b is moved radially inward. Accordingly, the position of the engagement part 91b of the first link 9b along the Y-axis is moved from the large-width groove 35b to a tapered groove 36b, and the engagement part 91b is guided to the small-width groove 37b by using the slopes of the tapered groove 36b and is engaged with the small-width groove 37b. In the medical manipulator 1, a change between the state in which the pivoting member 7 is not bent, which is shown in FIG. 2, and the state in which the pivoting member 7 is bent, which is shown in FIG. 3, is made through an operation of the handle 11.

Figure 4:
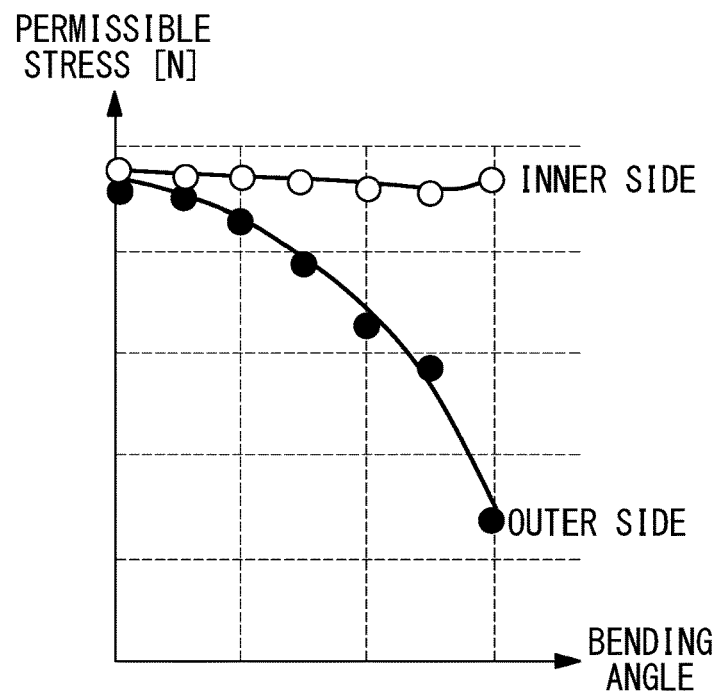
FIG. 4 is a graph showing the relationship between the bending angle and the permissible axial force, for each of an inner-side first link and an outer-side first link in the medical manipulator shown in FIG. 1.

FIG. 4 shows, in the case in which the pivoting member 7 is bent, the relationship of permissible stresses (permissible axial forces) on the link 8a, which is located at an inner side, and the link 8b, which is located at an outer side, with respect to the bending angle. As shown in FIG. 4, when the bending angle increases, the permissible axial force on the link 8b, which is located at the outer side of the bending, significantly decreases. On the other hand, even when the bending angle increases, the permissible axial force on the link 8a, which is located at the inner side of the bending, decreases only slightly. From this, it is found that, when the pivoting member 7 is bent, the link 8b, which is located at the outer side and the permissible stress of which is less, is more susceptible to damage than the link 8a, which is located at the inner side.

Figure 5:
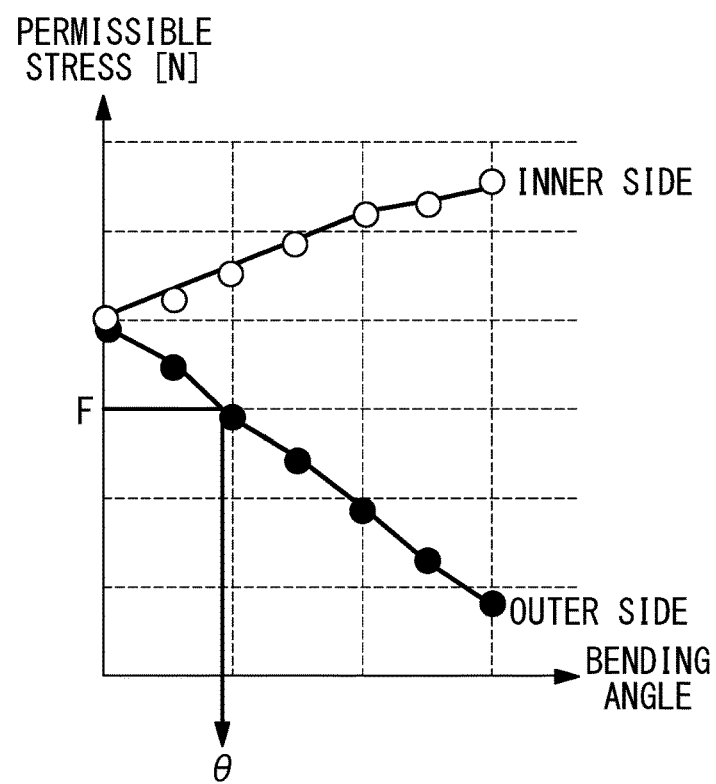
FIG. 5 is a graph showing the relationship between the bending angle and the permissible external force, for each of the inner-side first link and the outer-side first link in the medical manipulator shown in FIG. 1.

FIG. 5 shows, in a case in which an external force is applied to the pivoting member 7 when the pivoting member 7 is bent, the relationship of permissible external forces on the link 8a, which is located at the inner side, and the link 8b, which is located at the outer side, when an external force is concentrated thereon, with respect to the bending angle. As shown in FIG. 5, in a case in which an external force is concentrated on the link 8b, which is located at the outer side, the permissible external force on the link 8b significantly decreases when the bending angle increases. On the other hand, in a case in which an external force is concentrated on the link 8a, which is located at the inner side, the permissible external force on the link 8b increases, without decreasing, even when the bending angle increases. From this, it is found that, in a case in which an external force is concentrated on one of the links when the pivoting member 7 is bent, the link 8b, which is located at the outer side, is more susceptible to damage than the link 8a, which is located at the inner side.

As shown in FIG. 5, if it is attempted to set the permissible external forces to F Newtons (N) or greater, for example, the guide grooves 34a and 34b need to be formed such that, when the bending angle falls within the range from 0 degree to θ degree, the positions of the engagement parts 91a and 91b of the first links 9a and 9b along the Y-axis are located at the large-width grooves 35a and 35b.

The operations of the bending mechanism 5 and the medical manipulator 1 of this embodiment, which are thus configured, will be described below.

In order to perform treatment on an affected area by using the medical manipulator 1 of this embodiment, the insertion part 3 is inserted into the body, the treatment tool 2, which is mounted at the distal end, is disposed in the vicinity of the affected area, and the handle 11, which is provided in the operating part 4, is operated to make the pivoting member 7 pivot with respect to the support member 6, thereby adjusting the orientation of the treatment tool 2 with respect to the affected area.

As shown in FIG. 3, when the handle 11 is operated so as to be rotated, the two second links 14a and 14b, which are coupled to the handle 11 via the rack gears and the pinion gear, are moved along the X-axis. At this time, the groove cams 31a and 31b, which are fixed to the second links 14a and 14b via the fixing pins 38a and 38b, are moved along the X-axis. Because the engagement pins 32a and 33a on the groove cam 31a, which is fixed to the second link 14a moved toward the proximal end, are engaged with the slits 22a and 23a, the groove cam 31a, which is located in the Y-axis positive direction, is not moved along the Y-axis. As a result, because the engagement part 91a of the first link 9a is engaged with the small-width groove 37a of the guide groove 34a, the first link 9a is moved along the X-axis by the same amount of movement as the amount of movement of the second link 14a along the X-axis.

On the other hand, as shown in FIG. 3, because the engagement pins 32b and 33b on the groove cam 31b, which is fixed to the second link 14b moved toward the distal end, are engaged with the slits 22b and 23b, the groove cam 31b is moved radially outward. As a result, the position of the engagement part 91b of the first link 9b along the Y-axis is located at the large-width groove 35b of the guide groove 34b. Because the diameter of the engagement part 91b is less than the length of the large-width groove 35b along the X-axis, the first link 9b is not affected, within the predetermined range, by the amount of movement of the second link 14b along the X-axis. In other words, the first link 9b can be freely moved within the predetermined range along the X-axis.

Accordingly, in the state in which the medical manipulator 1 is bent, as shown in FIG. 3, when the treatment tool 2 comes into contact with something, for example, and receives an external force therefrom, the first link 9b can be moved within the predetermined range along the X-axis, irrespective of the amount of movement of the second link 14b. Specifically, because the first link 9b, which is located at the outer side, is not fixed in position, even if an external force is received, the first link 9b can be prevented from being damaged, through movement. On the other hand, the first link 9a, which is located at the inner side and the permissible stress of which is large, can transmit the movement along the X-axis, caused by the handle 11, to the pivoting member 7. As a result, in the medical manipulator 1, which has the bending mechanism 5 of this embodiment, it is possible to reduce damage to the first links 9a and 9b with respect to an external force, even in a state in which an operation of the handle 11 has been accepted.

Figure 6:
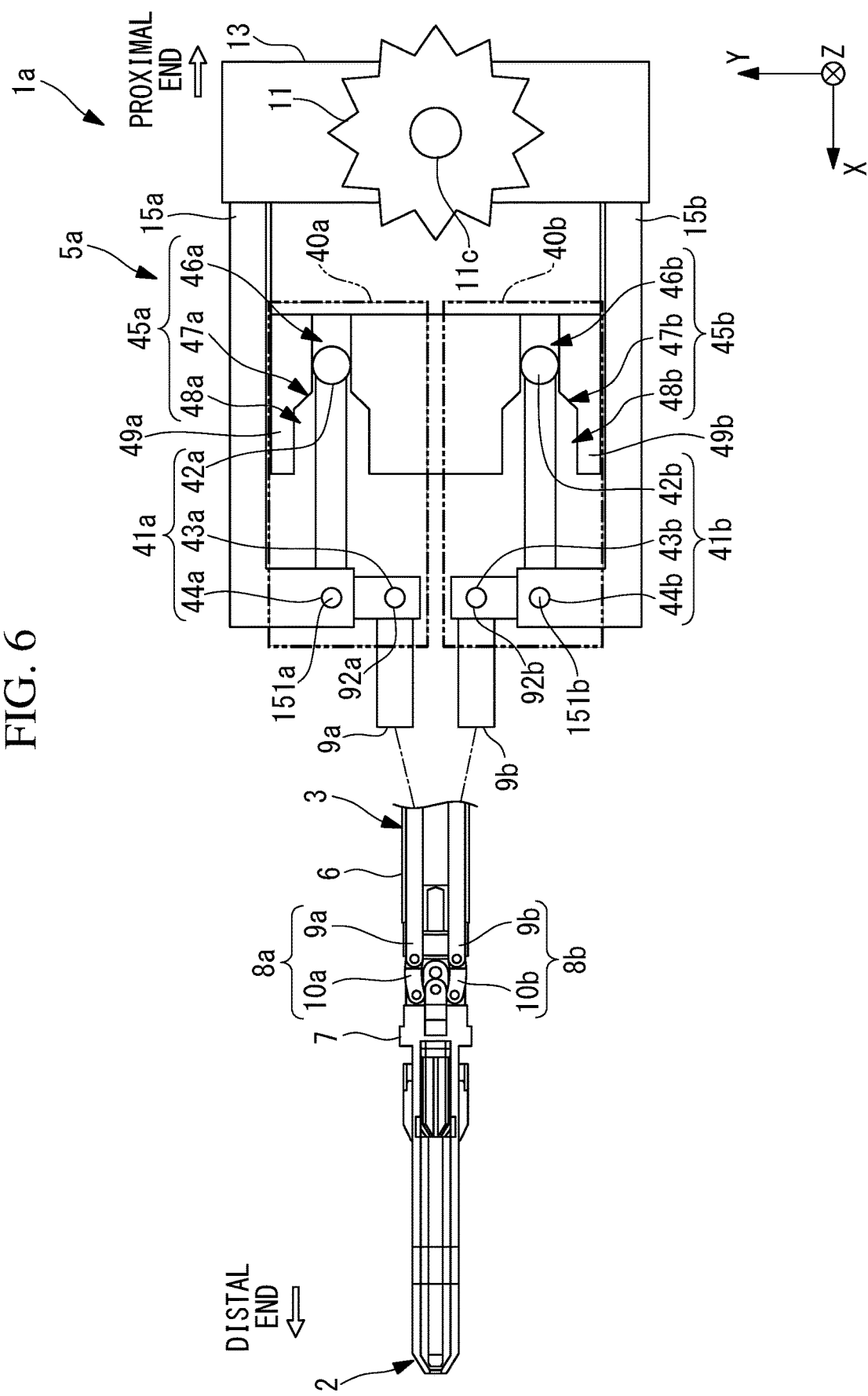
FIG. 6 is a sectional view showing a portion of a medical manipulator according to an exemplary embodiment, in a state in which the bending mechanism is not bent.

FIG. 6 shows a medical manipulator 1a that includes a bending mechanism 5a according to an exemplary embodiment. FIG. 6 shows a state in which the pivoting member 7 of the medical manipulator 1a is not bent. The medical manipulator 1a of this embodiment differs from the medical manipulator 1 of the above embodiment in terms of: second links 15a (first driving-force transmission member, proximal-end transmission member) and 15b (second driving-force transmission member, proximal-end transmission member); and coupling portions 40a and 40b. Thus, in this embodiment, parts different from those in the above embodiment will be described, and a description of parts identical to those therein will be omitted.

The second link 15a and 15b are fixed to the base 13, extend in the X-axis positive direction, and extend radially inward at the extended distal ends thereof. In the distal ends thereof, which are extended radially inward, circular holes 151a and 151b that are used to pivotably fix bellcranks 41a and 41b, to be described later, and that are parallel to the Z-axis are formed.

Because the respective coupling portions 40a and 40b are configured symmetrically about the ZX-plane that includes the central axis of the support member 6, in this embodiment, the coupling portion 40a will be described, and a description of the coupling portion 40b will be omitted. Reference signs of the coupling portion 40a and the coupling portion 40b differ only at the letters "a" and "b" appended to the reference signs, and the reference signs before the letters correspond to each other. The coupling portion 40a includes: the bellcrank 41a, which is fixed to the second link 15a so as to be pivotable in the XY-plane; a proximal-end fixing part 92a that is fixed to one end of the bellcrank 41a close to the distal end; and a groove cam 49a that is fixed to the base 13.

In the state shown in FIG. 6, the bellcrank 41a has a shape obtained by combining a cylindrical shape parallel to the X-axis and a cylindrical shape parallel to the Y-axis, which is perpendicular to the X-axis. A pivoting central axis (pivoting center) 44a is formed at the section where the two cylinders intersect. The pivoting central axis 44a is pivotably fixed in the circular hole 151a of the second link 15a. The bellcrank 41a has: a distal-end fixing part 43a at a radially inner side; and a spherical free end 42a that is engaged with the groove cam 49a, at the other end thereof with respect to the distal-end fixing part 43a. The distal-end fixing part 43a is fixed to the proximal-end fixing part 92a, which is formed on the first link 9a.

The groove cam 49a has a guide groove 45a that has, as the central axis, an axis parallel to the X-axis. The guide groove 45a has, in order from the proximal end, a small-width groove (restricting area) 46a, a tapered groove 47a, and a large-width groove (free-movement area) 48a. The small-width groove 46a has a fixed groove width that is slightly larger than the diameter of the free end 42a of the bellcrank 41a. The large-width groove 48a has a fixed groove width that is larger than the groove width of the small-width groove 46a. The tapered groove 47a is an inclined groove, the groove width of which gradually increases from the small-width groove 46a toward the large-width groove 48a.

As shown in FIG. 6, in the state in which the bending mechanism 5a is not bent, the free end 42a of the bellcrank 41a is engaged with the small-width groove 46a of the guide groove 45a. In the state in which the free end 42a is engaged with the small-width groove 46a, the bellcrank 41a cannot pivot about the pivoting central axis 44a. Thus, in this case, when the second link 15a is moved along the X-axis direction, the bellcrank 41a is moved along the X-axis by the same amount of movement as the second link 15a, without pivoting.

Figure 7:
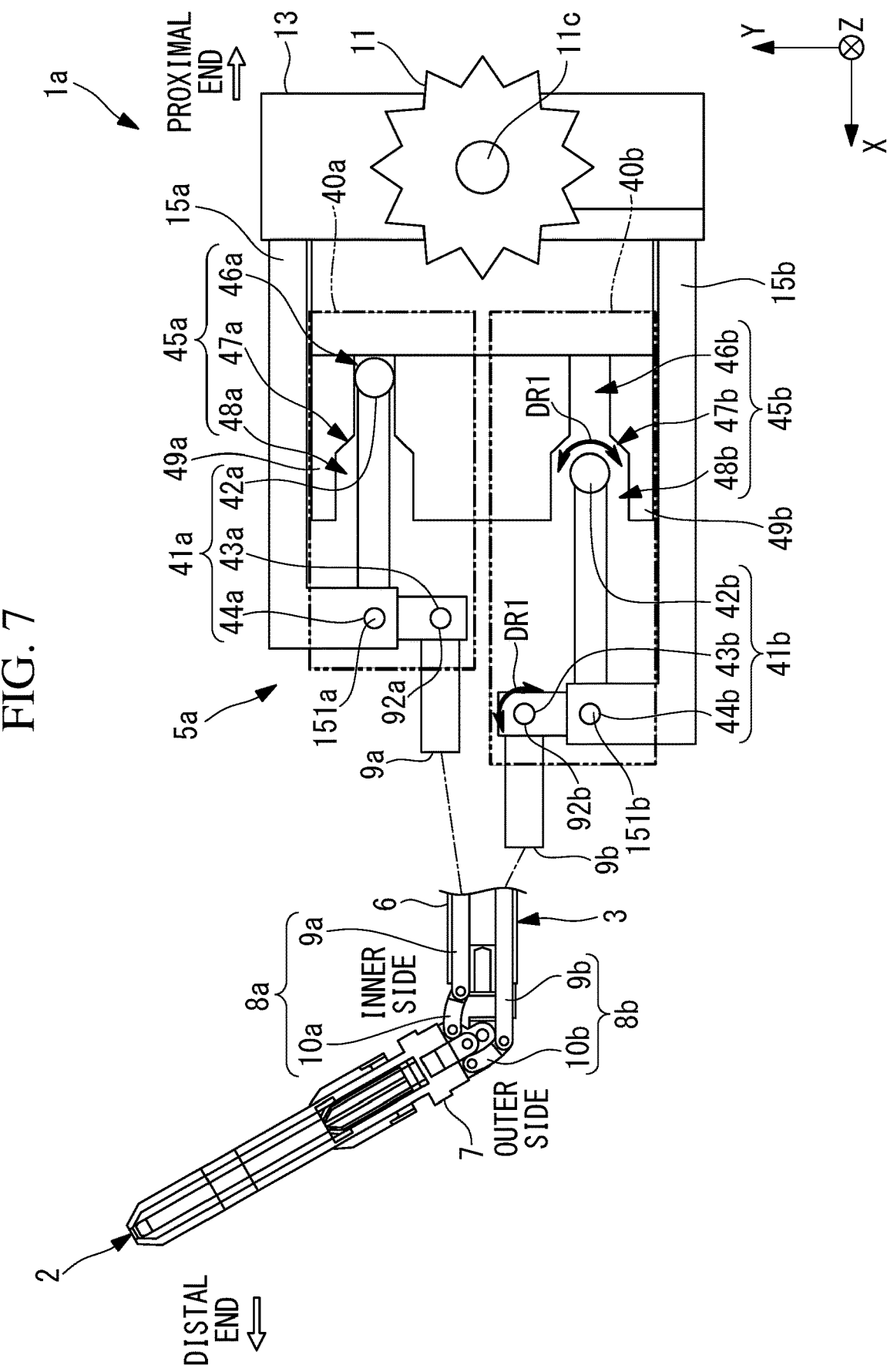
FIG. 7 is a sectional view showing the aforementioned portion of the medical manipulator according to an exemplary embodiment, in a state in which the bending mechanism is bent.

FIG. 7 shows the medical manipulator 1a when the handle 11 is rotated clockwise, thus bending the pivoting member 7. When the handle 11 is rotated clockwise, the second link 15a is moved toward the proximal end, and the second link 15b is moved toward the distal end. When the second link 15a is moved toward the proximal end, the bellcrank 41a, which is fixed at the circular hole 151a of the second link 15a, is moved toward the proximal end. In this case, the free end 42a of the bellcrank 41a is engaged with the small-width groove 46a of the guide groove 45a, as in the state shown in FIG. 6. Thus, the bellcrank 41a is moved toward the proximal end along the X-axis, without pivoting about the pivoting central axis 44a. Accordingly, the first link 9a, which is fixed to the distal-end fixing part 43a of the bellcrank 41a, is moved toward the proximal end along the X-axis by the same amount of movement as the amount of movement of the second link 15a along the X-axis.

When the handle 11 is rotated clockwise, and the second link 15b is moved toward the distal end, the bellcrank 41b, which is fixed at the circular hole 151b of the second link 15b, is moved toward the distal end. In this case, the position of a free end 42b of the bellcrank 41b along the X-axis is located at a large-width groove 48b of a guide groove 45b, unlike the state shown in FIG. 6. In this state, because the free end 42b of the bellcrank 41b is not fixed, the bellcrank 41b can be rotated about a pivoting central axis 44b along pivoting directions DR1. When the bellcrank 41b is rotated, the amount of movement by which the second link 15b is moved along the X-axis is different from the amount of movement by which the bellcrank 41b is moved along the X-axis. For example, when the bellcrank 41b pivots clockwise, the amount of movement by which the bellcrank 41a is moved along the X-axis is less than the amount of movement by which the second link 15b is moved along the X-axis.

In the bending mechanism 5a and the medical manipulator 1a of this embodiment, which are thus configured, when the handle 11 is operated so as to be rotated, as shown in FIG. 7, the second links 15a and 15b are moved along the X-axis. The bellcranks 41a and 41b, which are pivotably fixed to the second link 15a and 15b, are moved along the X-axis. As a result of the movement, when the position of the free end 42b of the bellcrank 41b along the X-axis is located at the large-width groove 48b of the guide groove 45b, the bellcrank 41b becomes pivotable about the pivoting central axis 44b.

As shown in FIG. 4, the permissible stress of the first link 9b, which is located at the outer side, becomes less as the bending angle of the bending mechanism 5a increases. In this case, the bellcrank 41b, which is fixed to the first link 9b at a distal-end fixing part 43b, can pivot within a predetermined range along the pivoting directions DR1. Thus, because the first link 9b, which is located at the outer side, is not fixed in position with respect to the second link 15b, even if an external force is received, the first link 9b can be prevented from being damaged, through movement within the predetermined range.

Third Embodiment

Figure 8:
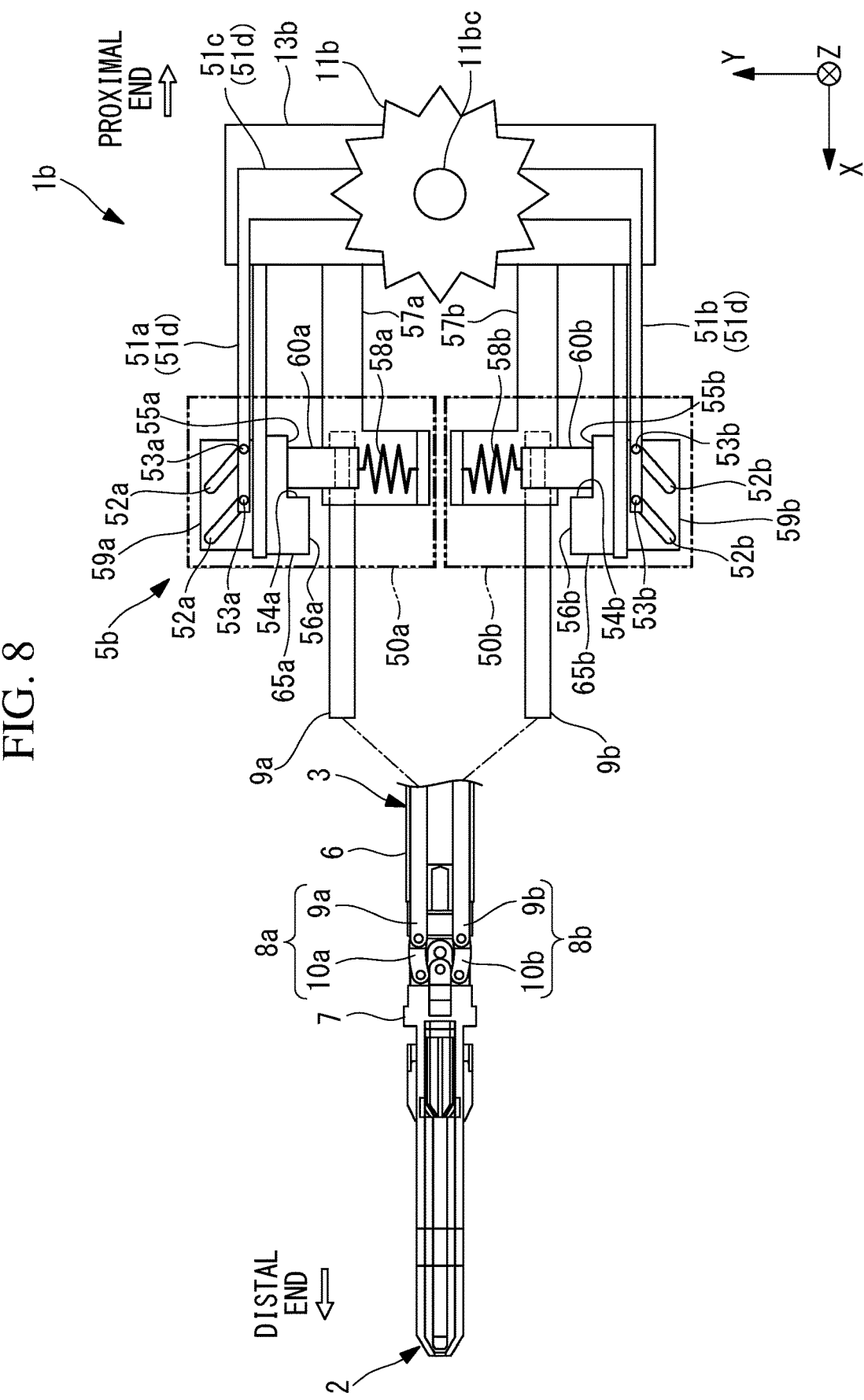
FIG. 8 is a sectional view showing a portion of a medical manipulator according to an exemplary embodiment, in a state in which the bending mechanism is not bent.

FIG. 8 shows a medical manipulator 1b that has a bending mechanism 5b according to an exemplary embodiment. FIG. 8 shows a state in which the pivoting member 7 of the medical manipulator 1b is not bent. The medical manipulator 1b of this embodiment differs from the medical manipulator 1 of the above embodiment shown in, for example, FIGS. 1-3, in terms of: a base 13b; a handle 11b; a pushing member 51d; a second link (first driving-force transmission member, proximal-end transmission member) 57a and a second link (second driving-force transmission member, proximal-end transmission member) 57b; and coupling portions 50a and 50b. Thus, in this embodiment, parts different from those in the above embodiment will be described, and a description of parts identical to those therein will be omitted.

The pushing member 51d, which can be moved along the X-axis, is attached to the base 13b. The pushing member 51d includes: a base section 51c on which the handle 11b is rotatably mounted; and coma-pusher pushing parts 51a and 51b that extend from the base section 51c toward the distal end. At the center of the base section 51c in the longitudinal direction along the Y-axis, a handle center shaft 11bc is mounted such that the handle 11b can be rotated about it. When the handle 11b is rotated about the handle center shaft 11bc, the second links 57a and 57b are moved along the X-axis.

One end of the coma-pusher pushing part 51a is attached to an end of the base section 51c in the Y-axis positive direction, and the coma-pusher pushing part 51a has, at a distal end thereof, two engagement pins 53a formed along the X-axis. Similarly, one end of the coma-pusher pushing part 51b is attached to an end of the base section 51c in the Y-axis negative direction, and the coma-pusher pushing part 51b has, at the distal end thereof, two engagement pins 53b formed along the X-axis.

Because the respective coupling portions 50a and 50b are configured symmetrically about the ZX-plane that includes the central axis of the support member 6, in this embodiment, the coupling portion 50a will be described, and a description of the coupling portion 50b will be omitted. Reference signs of the coupling portion 50a and the coupling portion 50b differ only at the letters "a" and "b" appended to the reference signs, and the reference signs before the letters correspond to each other.

The coupling portion 50a includes: a coma pusher 59a; a stopper member 65a that is connected to the coma pusher 59a; a coma 60a whose position along the X-axis is fixed at a radially inner side of the stopper member 65a; a biasing member 58a that biases the coma 60a radially outward; and a small-width section 93a (to be described later together with a description of FIG. 9) that is formed in the first link 9a and that is coupled to the coma 60a.

As shown in FIG. 8, the movement of the coma pusher 59a along the X-axis is regulated with respect to the base 13b. On the other hand, the coma pusher 59a can be moved along the Y-axis with respect to the base 13b. The coma pusher 59a has two slits 52a that are engaged with the two engagement pins 53a of the coma-pusher pushing part 51a. The slits 52a extend toward a radially outer side as the distances therefrom to the distal end decrease. Thus, when the pushing member 51d is moved toward the distal end, the coma pusher 59a is moved radially inward.

The stopper member 65a is fixed with respect to the base 13b. Thus, the coma pusher 59a can be moved in the Y-axis direction with respect to the stopper member 65a. The stopper member 65a has: a first surface 55a that is parallel to the ZX-plane and that is formed close to the proximal end; a second surface 56a that is parallel to the ZX-plane, that is formed close to the distal end, and that is formed closer to the radially inner side than the first surface 55a is; and a step surface 54a that connects the first surface 55a and the second surface 56a and that is parallel to the YZ-plane.

The coma 60a has a guide groove 64a (to be described later together with the description of FIG. 9) with which the proximal end of the first link 9*a* is engaged. A surface, of the coma 60*a*, that faces radially outward comes into contact with the first surface 55*a* of the stopper member 65*a* or a surface, of the coma pusher 59*a*, that faces radially inward, to be described later with reference to FIG. 10. In other words, the surface of the coma 60*a* facing radially outward comes into contact with, of the first surface 55*a* of the stopper member 65*a* and the surface of the coma pusher 59*a* facing radially inward, the surface that is located closer to the radially inner side. In the state shown in FIG. 8, the surface of the coma 60*a* facing radially outward is defined, in position along the Y-axis, by the first surface 55*a* of the stopper member 65*a*.

The second link 57*a* is supported by the base 13*b* so as to be linearly movable in the longitudinal direction of the link 8*a*, extends toward the distal end, and is moved along the X-axis direction. The biasing member 58*a* is fixed to the distal end of the second link 57*a*. The biasing member 58*a* is fixed to the coma 60*a*, at the opposite side of the biasing member 58*a* from the side thereof fixed to the second link 57*a*. The biasing member 58*a* biases the coma 60*a* radially outward.

Figure 9A:
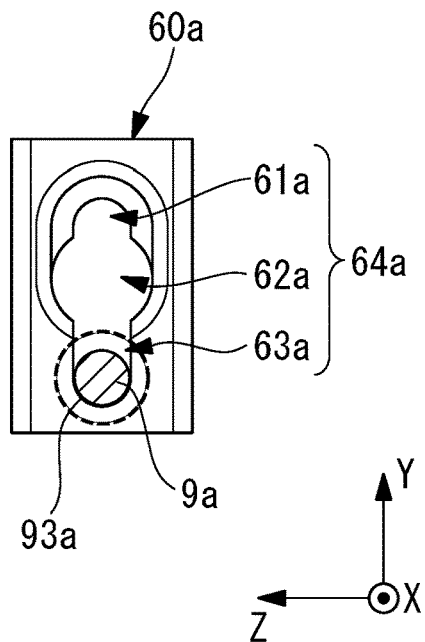
FIG. 9A is an explanatory view showing a positional relationship between a guide groove in a coma and the first link, in an exemplary embodiment.
Figure 9B:
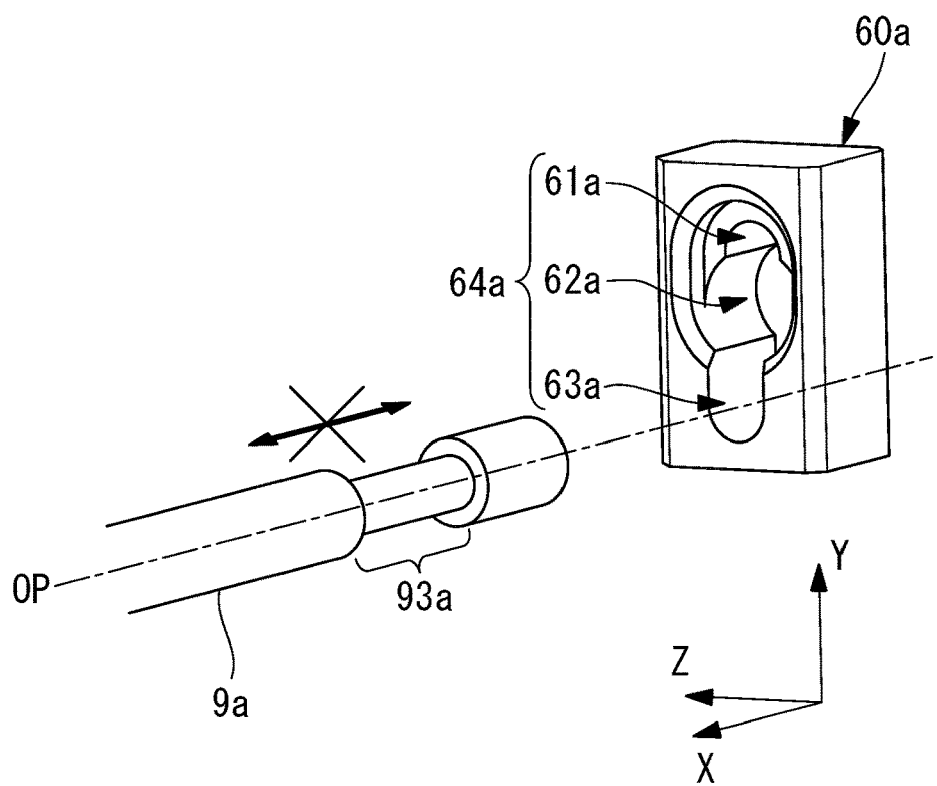
FIG. 9B is a perspective view showing the positional relationship between the guide groove in the coma and the first link, in an exemplary embodiment.

FIG. 9A shows an engagement relationship between the guide groove 64*a*, which is formed in the coma 60*a*, and the first link 9*a*, when the medical manipulator 1*b* is in the state shown in FIG. 8. As shown in FIG. 9A, the guide groove 64*a* has, in order from the radially inner side toward the radially outer side, a fixing groove (restricting area) 63*a*, a permissible groove (free-movement area) 62*a*, and a semi-fixing groove (semi-restricting area) 61*a*. Furthermore, as shown in FIG. 9B, compared with the other section of the first link 9*a*, the small-width section 93*a* of the first link 9*a* is reduced in diameter centered on a central axis OP of the first link 9*a* parallel to the X-axis. The length of the small-width section 93*a* along the X-axis is the same as the length of the fixing groove 63*a* along the X-axis. Thus, when the small-width section 93*a* is engaged with the fixing groove 63*a*, the first link 9*a* is fixed with respect to the coma 60*a*. A cross section of the fixing groove 63*a* in the YZ-plane has a substantially circular shape larger than the cross-sectional area of the first link 9*a*. Details of the semi-fixing groove 61*a* will be described later together with FIGS. 11 and 12.

When it is attempted to rotate the handle 11*b* in the state shown in FIG. 8 and FIG. 9A, although it is attempted to move the second links 57*a* and 57*b* along the X-axis, a surface of the coma 60*a* or a coma 60*b* facing toward the distal end is brought into contact with the step surface 54*a* or a step surface 54*b*. Thus, in the state shown in FIG. 8 and FIG. 9A, the handle 11*b* can hardly be rotated, so that the bending angle of the pivoting member 7 is small. In other words, this state is a regulated state where the pivoting member 7 is not freely bendable.

Figure 10:
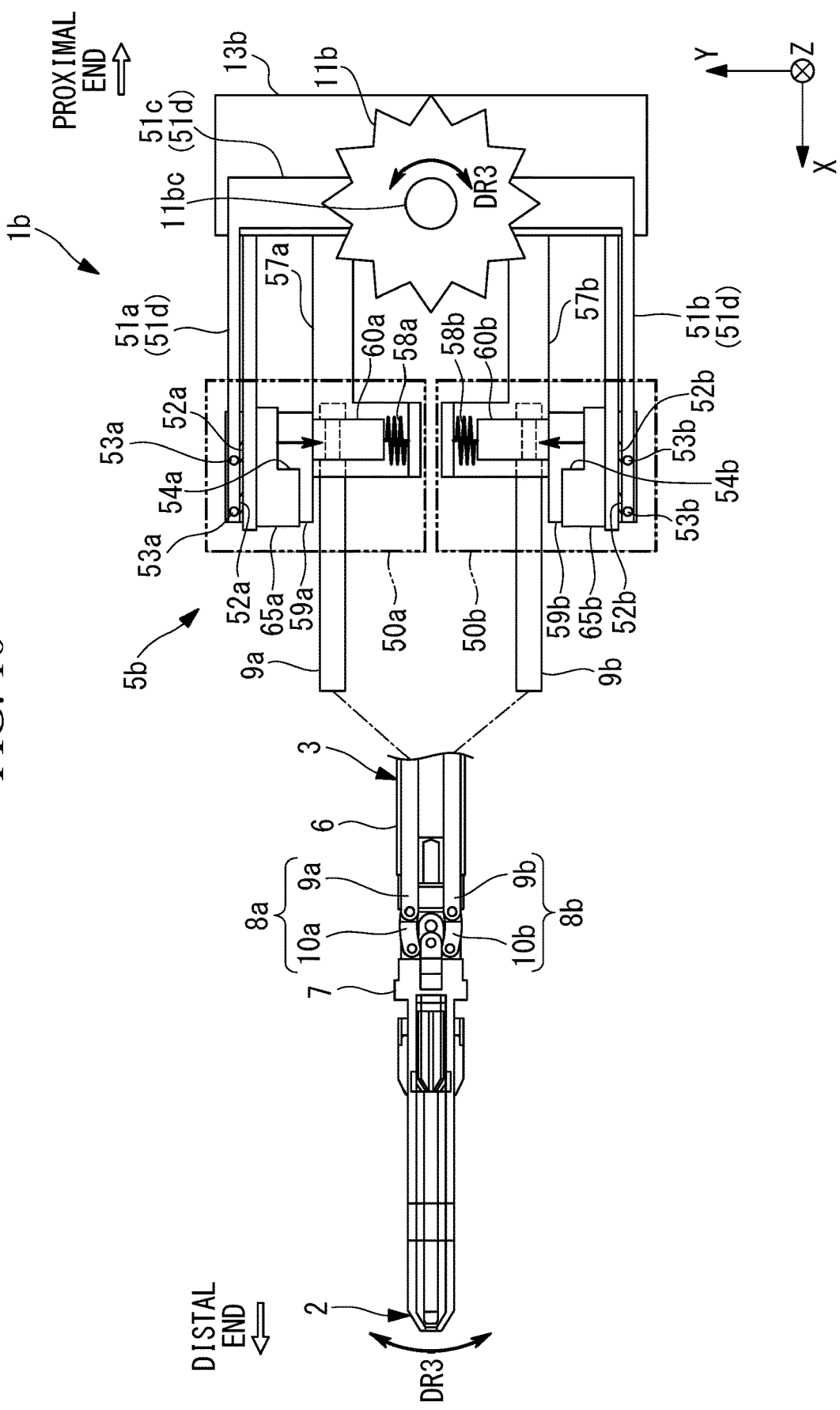
FIG. 10 is a sectional view showing the aforementioned portion of the medical manipulator of an exemplary embodiment, in a state in which a handle is pushed toward the distal end, thus allowing the bending mechanism to be bent.

FIG. 10 shows a state when a bending operation required for bending the pivoting member 7 by a large amount is performed. In the medical manipulator 1*b* of this embodiment, in order to bend the pivoting member 7, it is necessary to move the handle 11*b* toward the distal end with respect to the base 13*b*. Compared with the state shown in FIG. 8, the handle 11*b* and the pushing member 51*d* shown in FIG. 10 are moved toward the distal end with respect to the base 13*b*. When the pushing member 51*d* is moved toward the distal end, the engagement pins 53*a* and 53*b* of the pushing member 51*d* are moved toward the distal end along the slits 52*a* and slits 52*b* of the coma pusher 59*a* and a coma pusher 59*b*. Accordingly, because the coma pushers 59*a* and 59*b* can be moved along the Y-axis, the coma pushers 59*a* and 59*b* are moved radially inward.

In the state shown in FIG. 10, unlike the state shown in FIG. 8, the surfaces of the comas 60*a* and 60*b* facing radially outward are brought into contact with the surfaces of the coma pushers 59*a* and 59*b* facing radially inward. Specifically, the positions of the comas 60*a* and 60*b* along the Y-axis are defined by the coma pushers 59*a* and 59*b* that have been moved radially inward.

Figure 11A:
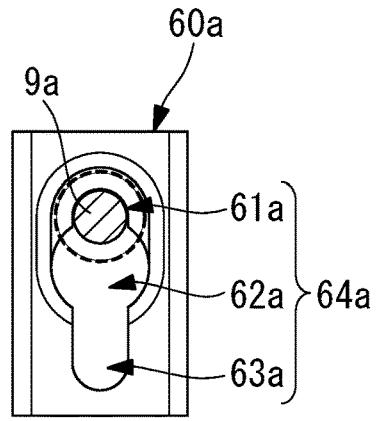
FIG. 11A is an explanatory view showing a positional relationship between the guide groove in the coma and the first link, in an exemplary embodiment.
Figure 11B:
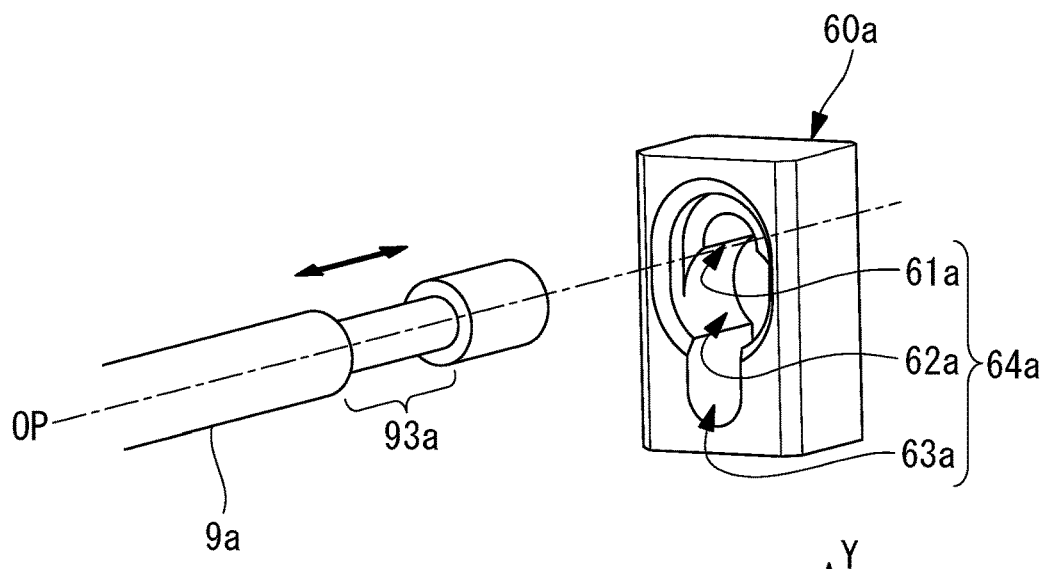
FIG. 11B is a perspective view showing the positional relationship between the guide groove in the coma and the first link, in an exemplary embodiment.

When the comas 60*a* and 60*b* are moved radially inward, the positions of the first links 9*a* and 9*b* along the Y-axis change with respect to the guide groove 64*a* and a guide groove 64*b* in the comas 60*a* and 60*b*. FIGS. 11A and 11B show an engagement relationship between the guide groove 64*a*, which is formed in the coma 60*a*, and the first link 9*a*, when the medical manipulator 1 is in the state shown in FIG. 10. As shown in FIGS. 11A and 11B, the small-width section 93*a* of the first link 9*a* is engaged with the semi-fixing groove 61*a*.

Figure 12:
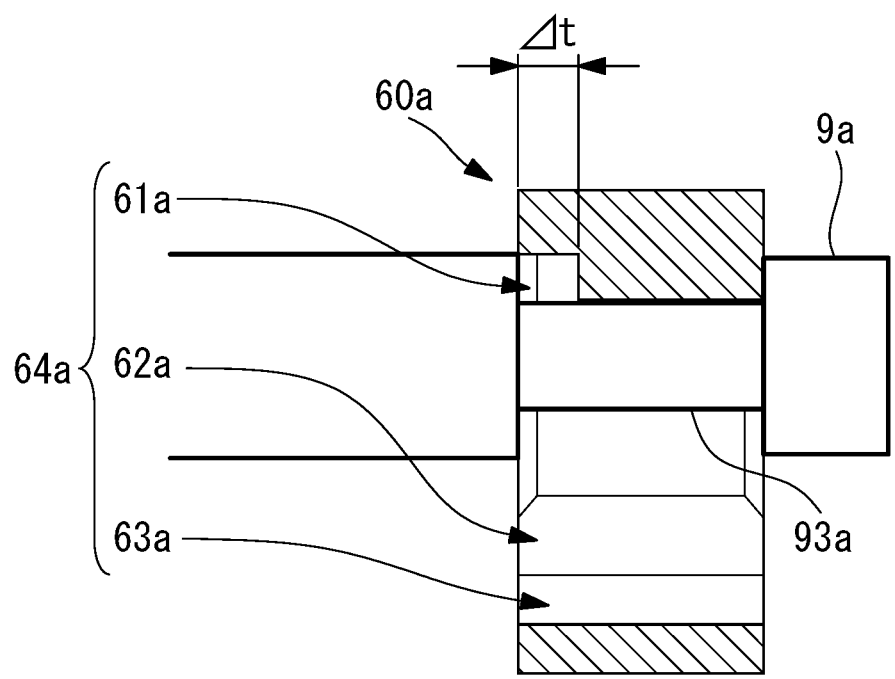
FIG. 12 is a sectional view showing the positional relationship between the guide groove in the coma and the first link, shown in FIG. 11A.

FIG. 12 is a sectional view, parallel to the XY-plane, showing a case in which the small-width section 93*a* is engaged with the semi-fixing groove 61*a*. As shown in FIGS. 11A and 11B and FIG. 12, the semi-fixing groove 61*a* has: a substantially cylinder-shaped section that is formed close to the proximal end and that has the same diameter as that of the small-width section 93*a*; and a substantially cylinder-shaped section that is formed close to the distal end and that has the same diameter as the cross-sectional area of the first link 9*a*, which has a larger diameter than the small-width section 93*a*. In the semi-fixing groove 61*a*, the large-diameter section is present for a distance Δt so as to allow a large-diameter section of the first link 9*a* to be moved along the X-axis. In this embodiment, the movement distance of the second link 57*a* along the X-axis and the movement distance of the second link 57*b* along the X-axis are in a symmetrical relationship. On the other hand, when the pivoting member 7 is bent, the movement distance of the first link 9*a* along the X-axis and the movement distance of the first link 9*b* along the X-axis are not in a symmetrical relationship. Thus, by providing the gap for the distance Δt in the semi-fixing groove 61*a*, the difference in the movement distance between the first links 9*a* and 9*b* and the second links 57*a* and 57*b* is absorbed. In the state shown in FIGS. 11A and 11B and FIG. 12, the difference between the amount of movement of the first link 9*a* along the X-axis and the amount of movement of the first link 9*b* along the X-axis falls within a predetermined range.

In the state shown in FIG. 10, due to the biasing forces of the biasing member 58*a* and a biasing member 58*b*, forces that push back the coma pushers 59*a* and 59*b* radially outward act. Because the slits 52*a* and 52*b* in the coma pushers 59*a* and 59*b* and the engagement pins 53*a* and 53*b* of the coma-pusher pushing parts 51*a* and 51*b* are engaged with each other, the pushing member 51*d* receives a force that pushes the pushing member 51*d* toward the proximal end. Accordingly, the handle 11*b* receives the force that pushes the handle 11*b* toward the proximal end.

Figure 13:
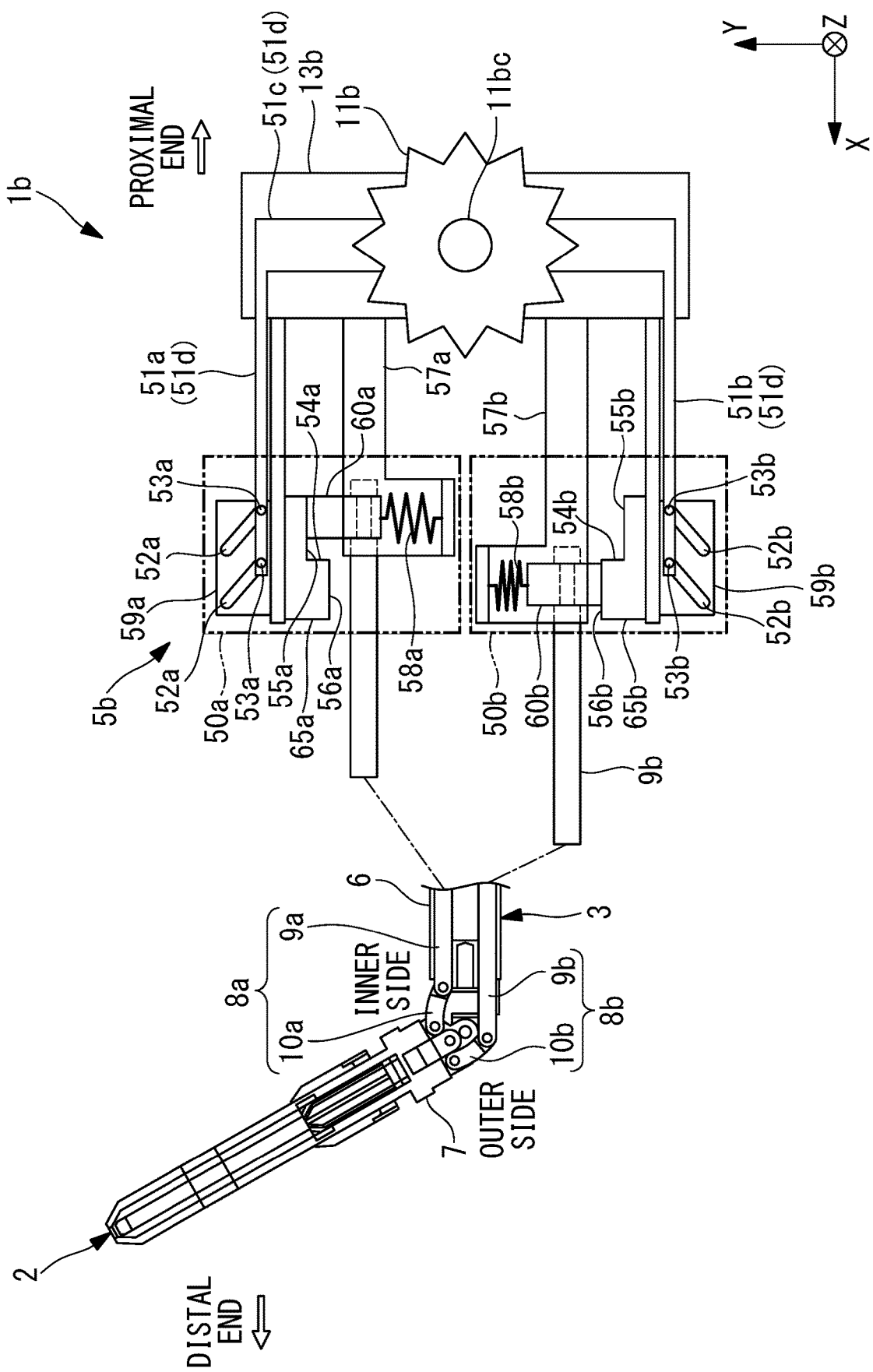
FIG. 13 is a sectional view showing the aforementioned portion of the medical manipulator of an exemplary embodiment, in a state in which the bending mechanism is bent.

In this state, when the handle 11*b* is gradually moved toward the proximal end, and the handle 11*b* is rotated, for example, clockwise, before the coma pusher 59*b* returns to the position at the radially outer side, which is shown in FIG. 8, the coma 60*b* is moved over the step surface 54*b* of a stopper member 65*b* and is moved to the position on a second surface 56*b* of the stopper member 65*b*, as shown in FIG. 13. In contrast to this, the coma 60*a* is moved to the position on the first surface 55*a* of the stopper member 65*a*.

In this case, the small-width section 93*a* of the first link 9*a* is engaged with the fixing groove 63*a* of the guide groove 64*a*, as in the state shown in FIGS. 8 and 9A. On the other hand, in the state shown in FIG. 13, the section of the guide groove 64b with which the first link 9b is engaged is different from that in the state shown in FIGS. 8 and 9.

Figure 14A:
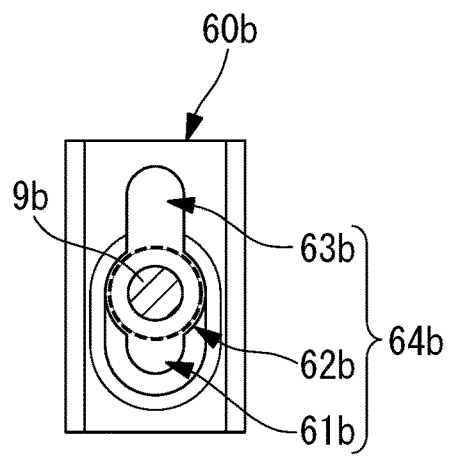
FIG. 14A is an explanatory view showing the positional relationship between the guide groove in the coma and the first link, in an exemplary embodiment.
Figure 14B:
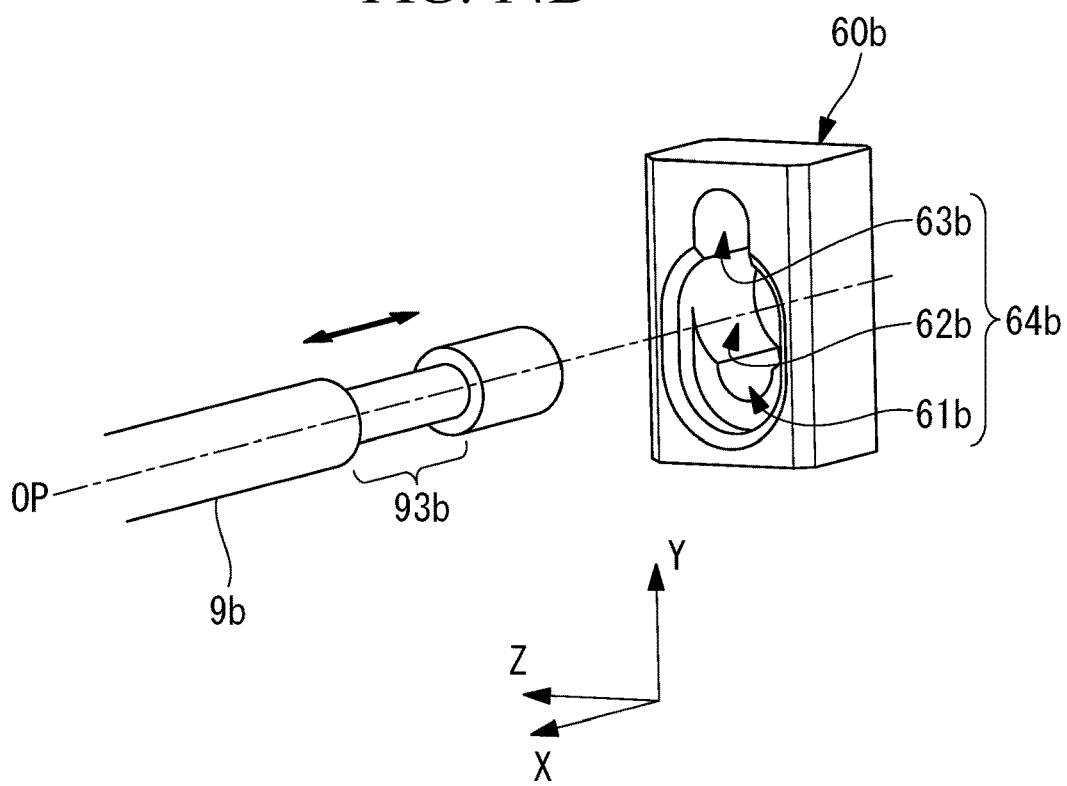
FIG. 14B is a perspective view showing the positional relationship between the guide groove in the coma and the first link, in an exemplary embodiment.

FIGS. 14A and 14B show an engagement relationship between the guide groove 64b, which is formed in the coma 60b, and the first link 9b, when the medical manipulator 1 is in the state shown in FIG. 13. As shown in FIG. 14A, the position of a small-width section 93b of the first link 9b along the Y-axis is located in a permissible groove 62b. Thus, when the first link 9b is moved along the X-axis direction, because the first link 9b does not come into contact with the coma 60b, the engagement pins 53b can be freely moved inside the slits 52b along the X-axis within the movable ranges. Specifically, in this embodiment, in order to bend the pivoting member 7, in the regulated state where the handle 11b can hardly be rotated, which is shown in FIG. 8, the handle 11b undergoes a release operation for moving the handle 11b toward the distal end, as shown in FIG. 10, thereby releasing the handle 11b from the regulated state. Then, the handle 11b becomes able to be rotated, and, in the state shown in FIG. 13, the pivoting member 7 is switched to a pivotable state.

In the bending mechanism 5b and the medical manipulator 1b of this embodiment, which are thus configured, when the pivoting member 7 is not bent, as shown in FIG. 8, even if the handle 11b is rotated, the positions of the comas 60a and 60b along the X-axis are regulated by the step surfaces 54a and 54b of the stopper members 65a and 65b. Thus, the first links 9a and 9b, which are coupled to the comas 60a and 60b, can hardly be moved along the X-axis. From this state, as in the state shown in FIG. 10, when the handle 11b is pushed toward the distal end, the coma pushers 59a and 59b are moved radially inward, and the comas 60a and 60b are also moved radially inward. When the handle 11b is rotated from this state, because the comas 60a and 60b are not regulated by the step surfaces 54a and 54b of the stopper members 65a and 65b, the comas 60a and 60b can be moved within the predetermined ranges along the X-axis. Accordingly, the first links 9a and 9b, which are coupled to the comas 60a and 60b, can be moved along the X-axis, thus making it possible to bend the pivoting member 7.

In the state shown in FIG. 13, in which the pivoting member 7 is bent, the permissible stress of the first link 9b, which is located at the outer side of the bending, is reduced more than the first link 9a, which is located at the inner side of the bending, as shown in the graph of FIG. 4. However, in the medical manipulator 1b of this embodiment, the position of the first link 9b, which is located at the outer side, along the X-axis is not regulated by the coma 60b. Thus, even when an external force is applied to the pivoting member 7, only the first link 9a, which is located at the inner side and the permissible stress of which is large, receives the external force, and the first link 9b, which is located at the outer side, need not receive the external force. Accordingly, it is possible to reduce damage to the first links 9a and 9b.

Fourth Embodiment

Figure 15:
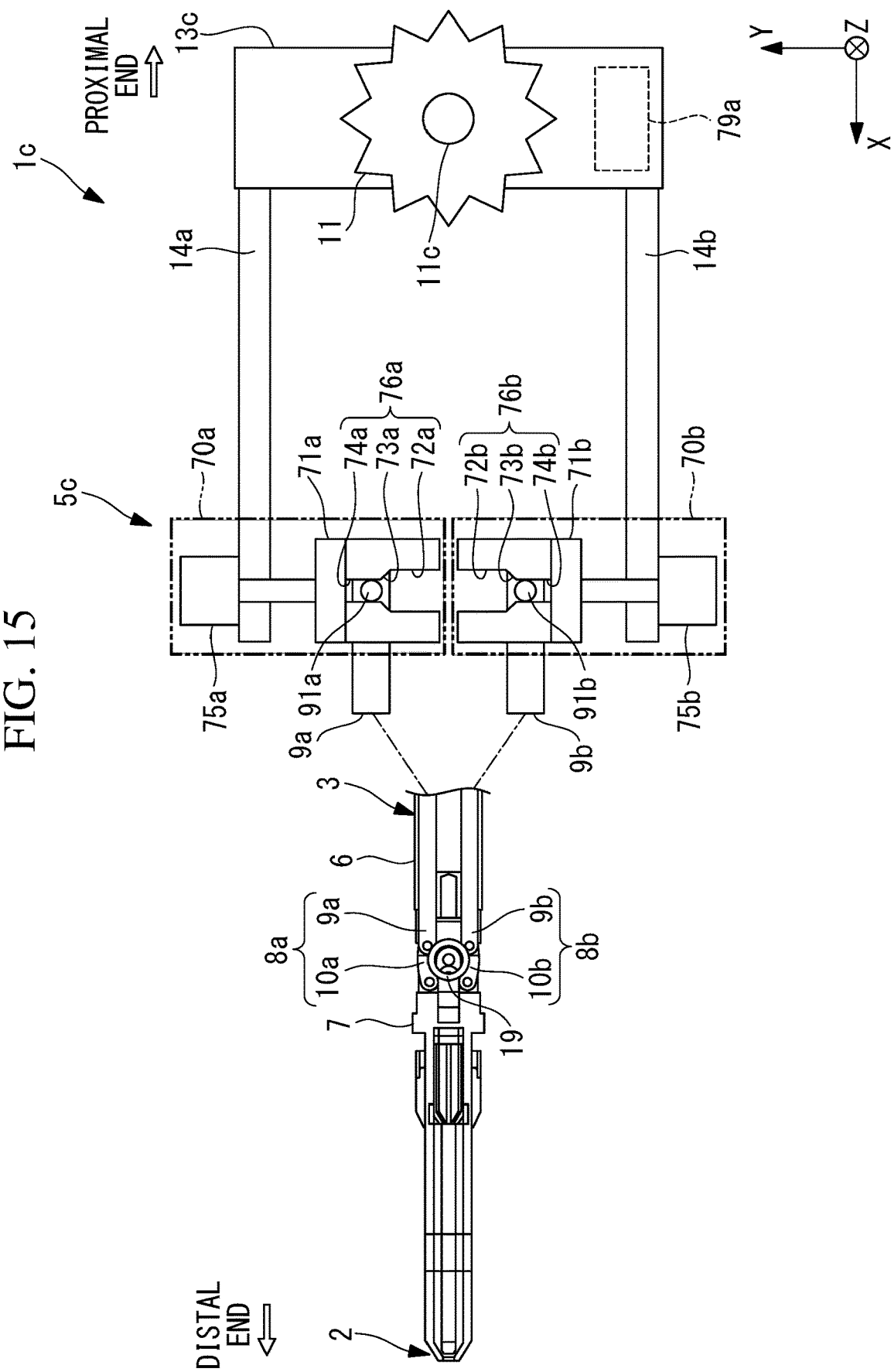
FIG. 15 is a sectional view showing a portion of a medical manipulator according to an exemplary embodiment, in a state in which the bending mechanism is not bent.

FIG. 15 shows a medical manipulator 1c that includes a bending mechanism 5c according to an exemplary embodiment. FIG. 15 shows a state in which the pivoting member 7 of the medical manipulator 1c is not bent. The medical manipulator 1c of this embodiment differs from the medical manipulator 1 of the above embodiment shown in, for example, FIGS. 1-3, in that a rotary encoder 19 is provided, a base 13c has a control unit 79a, and coupling portions 70a and 70b are provided. Thus, in this embodiment, parts different from those in the above embodiment will be described, and a description of parts identical to those therein will be omitted.

As shown in FIG. 15, the rotary encoder 19 is disposed between the short link 10a and the short link 10b. The rotary encoder 19 detects a bending angle when the bending mechanism 5c is bent. The detected bending angle is processed by the control unit 79a, which is built into the base 13c.

Because the respective coupling portions 70a and 70b are configured symmetrically about the ZX-plane that includes the central axis of the support member 6, in this embodiment, the coupling portion 70a will be described, and a description of the coupling portion 70b will be omitted. Reference signs of the coupling portion 70a and the coupling portion 70b differ only at the letters "a" and "b" appended to the reference signs, and the reference signs before the letters correspond to each other. The coupling portion 70a includes: an actuator 75a that is fixed at the distal end of the second link 14a; a groove cam 71a that is fixed to a radially inner side of the actuator 75a and that has a guide groove 76a; and an engagement part 91a that is formed on the first link 9a and that is engaged with the guide groove 76a.

The actuator 75a changes the position of the groove cam 71a along the Y-axis with respect to the second link 14a, on the basis of a control signal received from the control unit 79a. Specifically, on the basis of a control signal from the control unit 79a, the actuator 75a does not change the position of the groove cam 71a along the Y-axis when the pivoting member 7 is bent in the Y-axis positive direction (upward in FIG. 15). On the basis of a control signal from the control unit 79a, the actuator 75a changes the position of the groove cam 71a along the Y-axis, radially inward when the pivoting member 7 is bent in the Y-axis negative direction (downward in FIG. 15).

The groove cam 71a has the guide groove 76a, which has the same shape as the guide groove 34a in the above embodiment. The guide groove 76a has a small-width groove (restricting area) 74a, a tapered groove 73a, and a large-width groove (free-movement area) 72a. The engagement part 91a of the first link 9a is engaged with the guide groove 76a of the groove cam 71a. Note that the first link 9a that includes the engagement part 91a in this embodiment is the same as that in the above embodiment shown in, for example, FIGS. 1-3. In the state shown in FIG. 15, where the pivoting member 7 does not pivot, the engagement part 91a is engaged with the small-width groove 74a.

Figure 16:
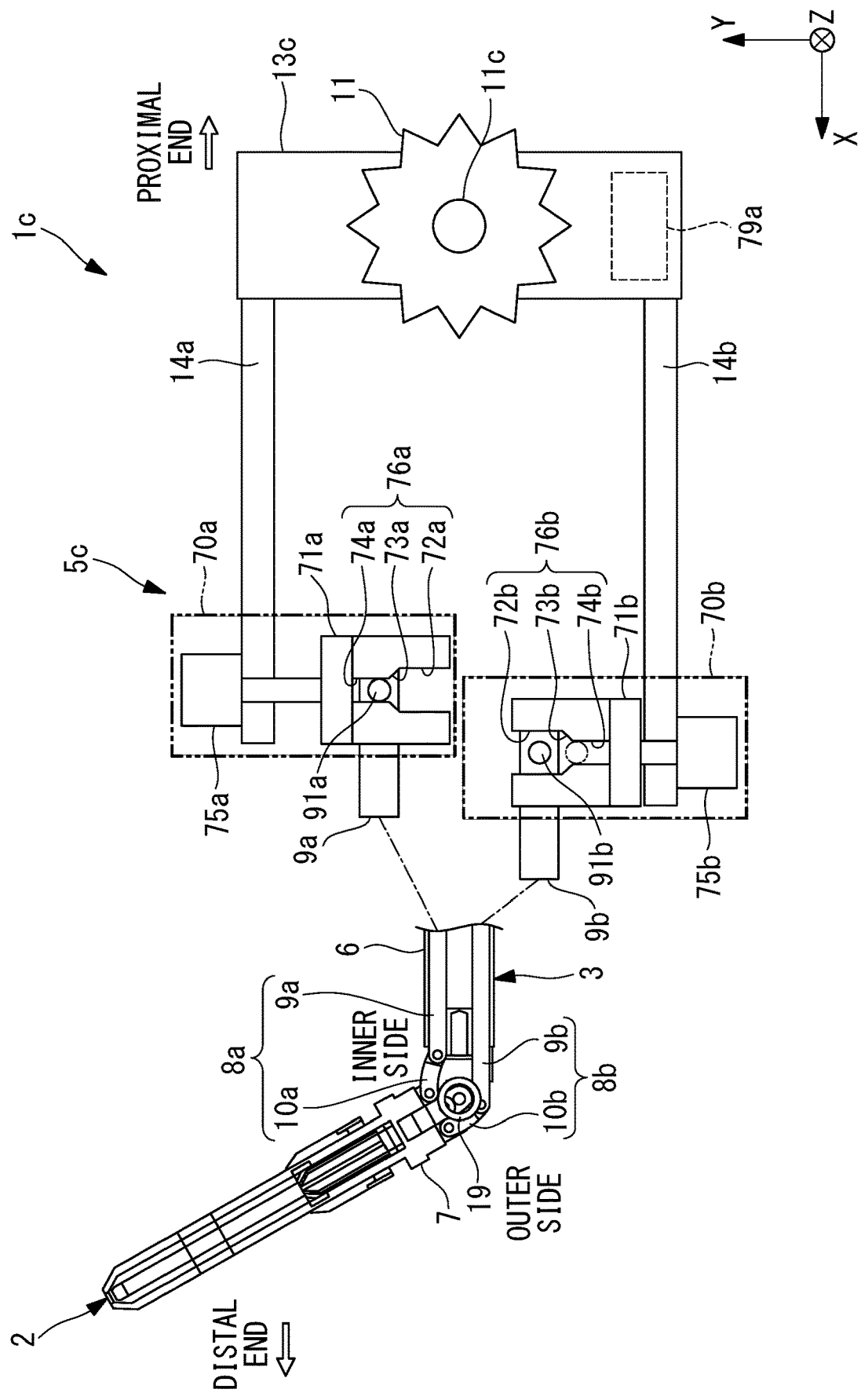
FIG. 16 is a sectional view showing the aforementioned portion of the medical manipulator of an exemplary embodiment, in a state in which the bending mechanism is bent.

FIG. 16 shows the medical manipulator 1c in a state where the handle 11 is rotated clockwise, thus bending the pivoting member 7. When the handle 11 is rotated clockwise from the state shown in FIG. 15, the second link 14a is moved toward the proximal end, and the second link 14b is moved toward the distal end. Because the engagement parts 91a and 91b of the first links 9a and 9b are engaged with the small-width groove 74a and a small-width groove 74b of the guide groove 76a and a guide groove 76b, the first links 9a and 9b are moved along the X-axis in response to the movement of the second links 14a and 14b. Accordingly, as shown in FIG. 16, the pivoting member 7 is bent.

When the pivoting member 7 is bent, the rotary encoder 19 detects the bending angle of the pivoting member 7. The control unit 79a controls an actuator 75b that is coupled to the first link 9b, which is located at the outer side, on the basis of the detected bending angle. In this embodiment, θ degree is set as a threshold for the bending angle, and, when the bending angle exceeds the threshold, the position of the engagement part 91b of the first link 9b, which is located at the outer side, along the Y-axis is set so as to be located in a large-width groove 72b of the guide groove 76b. In the state shown in FIG. 16, because the bending angle of the pivoting member 7 has exceeded the threshold, the control unit 79a moves a groove cam 71b radially outward. Accordingly, the position of the engagement part 91b along the Y-axis is located in the large-width groove 72b.

In the bending mechanism 5c and the medical manipulator 1c of this embodiment, which are thus configured, when the handle 11 is rotated, as shown in FIG. 16, the respective second links 14a and 14b are symmetrically moved along the X-axis. When the second links 14a and 14b are moved, the pivoting member 7 is bent, and the rotary encoder 19 detects the bending angle. When the detected bending angle exceeds the threshold, the control unit 79a moves the actuator 75a or the actuator 75b radially outward. Accordingly, the position of the engagement part 91a of the first link 9a or the engagement part 91b of the first link 9b along the Y-axis with respect to the guide groove 76a or 76b changes to the large-width groove 72a or the large-width groove 72b. Thus, because the first link 9a or the first link 9b that is located at the outer side of the bending and the permissible stress of which is less need not receive an external force, damage to the first links 9a and 9b is reduced.

Fifth Embodiment

Figure 17:
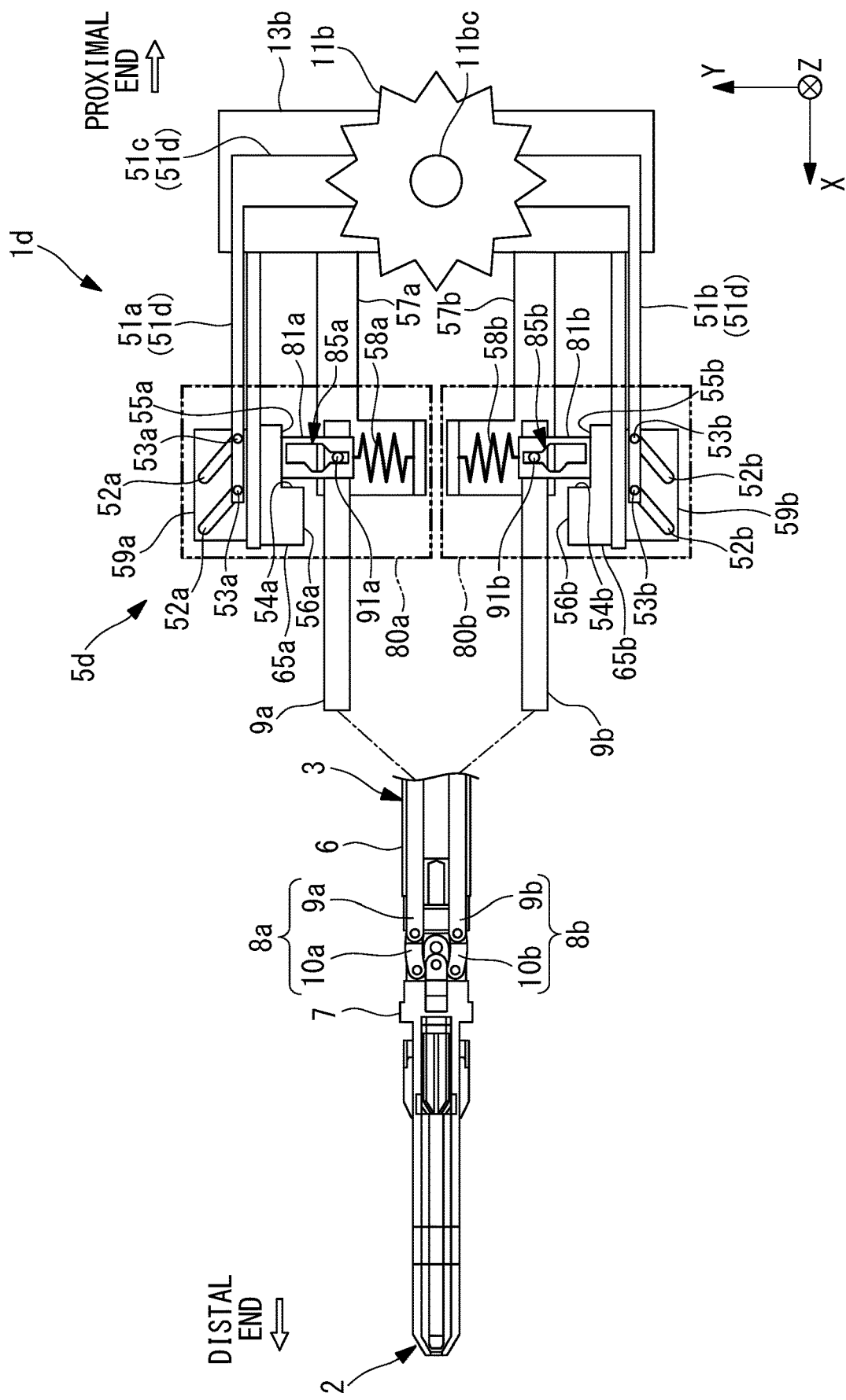
FIG. 17 is a sectional view showing a portion of a medical manipulator according to an exemplary embodiment, in a state in which the bending mechanism is not bent.

FIG. 17 shows a medical manipulator 1d that includes a bending mechanism 5d according to an exemplary embodiment. FIG. 17 shows a state in which the pivoting member 7 of the medical manipulator 1d is not bent. The medical manipulator 1d of this embodiment differs from the medical manipulator 1b of the above embodiment shown in, for example, FIGS. 8-14B, in terms of: groove cams 81a and 81b that are included in coupling portions 80a and 80b; and engagement parts 91a and 91b of the first links 9a and 9b, which are coupled to the groove cams 81a and 81b. In particular, this embodiment significantly differs from the above embodiment shown in, for example, FIGS. 8-14B, in that the groove cams 81a and 81b are used instead of the comas 60a and 60b of the above embodiment. Thus, in this embodiment, parts different from those in the above embodiment will be described, and a description of parts identical to those therein will be omitted.

Because the respective coupling portions 80a and 80b are configured symmetrically about the ZX-plane that includes the central axis of the support member 6, in this embodiment, the coupling portion 80a will be described, and a description of the coupling portion 80b will be omitted. Reference signs of the coupling portion 80a and the coupling portion 80b differ only at the letters "a" and "b" appended to the reference signs, and the reference signs before the letters correspond to each other.

The coupling portion 80a includes: the groove cam 81a, which is fixed to a radially inner side of the stopper member 65a; and the engagement part 91a of the first link 9a, which is engaged with a guide groove 85a that is formed in the groove cam 81a.

A surface, of the groove cam 81a, that faces radially outward comes into contact with the first surface 55a of the stopper member 65a or a surface, of the coma pusher 59a, that faces radially inward, to be described later with reference to FIG. 19. Specifically, the surface, of the groove cam 81a, facing radially outward comes into contact with, of the first surface 55a of the stopper member 65a and the surface of the coma pusher 59a facing radially inward, the surface that is located closer to the radially inner side. In the state shown in FIG. 17, the surface of the groove cam 81a facing radially outward is defined, in the position thereof along the Y-axis, by the first surface 55a of the stopper member 65a.

FIG. 18 shows an engagement relationship between the guide groove 85a, which is formed in the groove cam 81a, and the engagement part 91a of the first link 9a when the medical manipulator 1d is in the state shown in FIG. 17. As shown in FIG. 18, the guide groove 85a has, in order from the radially inner side toward the radially outer side, a fixing groove (restricting area) 84a, a both-side tapered groove 87a, a permissible groove (free-movement area) 83a, a one-side tapered groove 86a, and a semi-fixing groove (semi-restricting area) 82a.

The fixing groove 84a has a rectangular cross section having, in the ZX-plane, fixed lengths along the X-axis and the Z-axis. The permissible groove 83a has a rectangular cross section that has a length extending, along the X-axis, further toward the distal end and the proximal end than the length of the fixing groove 84a. The length of the fixing groove 84a along the X-axis is the same as the diameter of the engagement part 91a of the first link 9a. The semi-fixing groove 82a has a rectangular cross section that has a length extending, along the X-axis, further only toward the proximal end than the length of the fixing groove 84a. The both-side tapered groove 87a has an inclined cross section whose rectangular cross-sectional area gradually increases from the fixing groove 84a toward the permissible groove 83a. The one-side tapered groove 86a has an inclined cross section whose rectangular cross-sectional area gradually decreases from the permissible groove 83a toward the semi-fixing groove 82a.

In the state shown in FIGS. 17 and 18, because the engagement part 91a of the first link 9a is engaged with the fixing groove 84a of the guide groove 85a, the amount of movement of the second link 57a along the X-axis is the same as the amount of movement of the first link 9a along the X-axis. When it is attempted to rotate the handle 11b in this state, in the second link 57a or 57b, the surface of the groove cam 81a or the groove cam 81b facing toward the distal end comes into contact with the step surface 54a or the step surface 54b. Thus, in the state shown in FIGS. 17 and 18, even when the handle 11b is rotated, the bendable angle of the pivoting member 7 is small.

Figure 19:
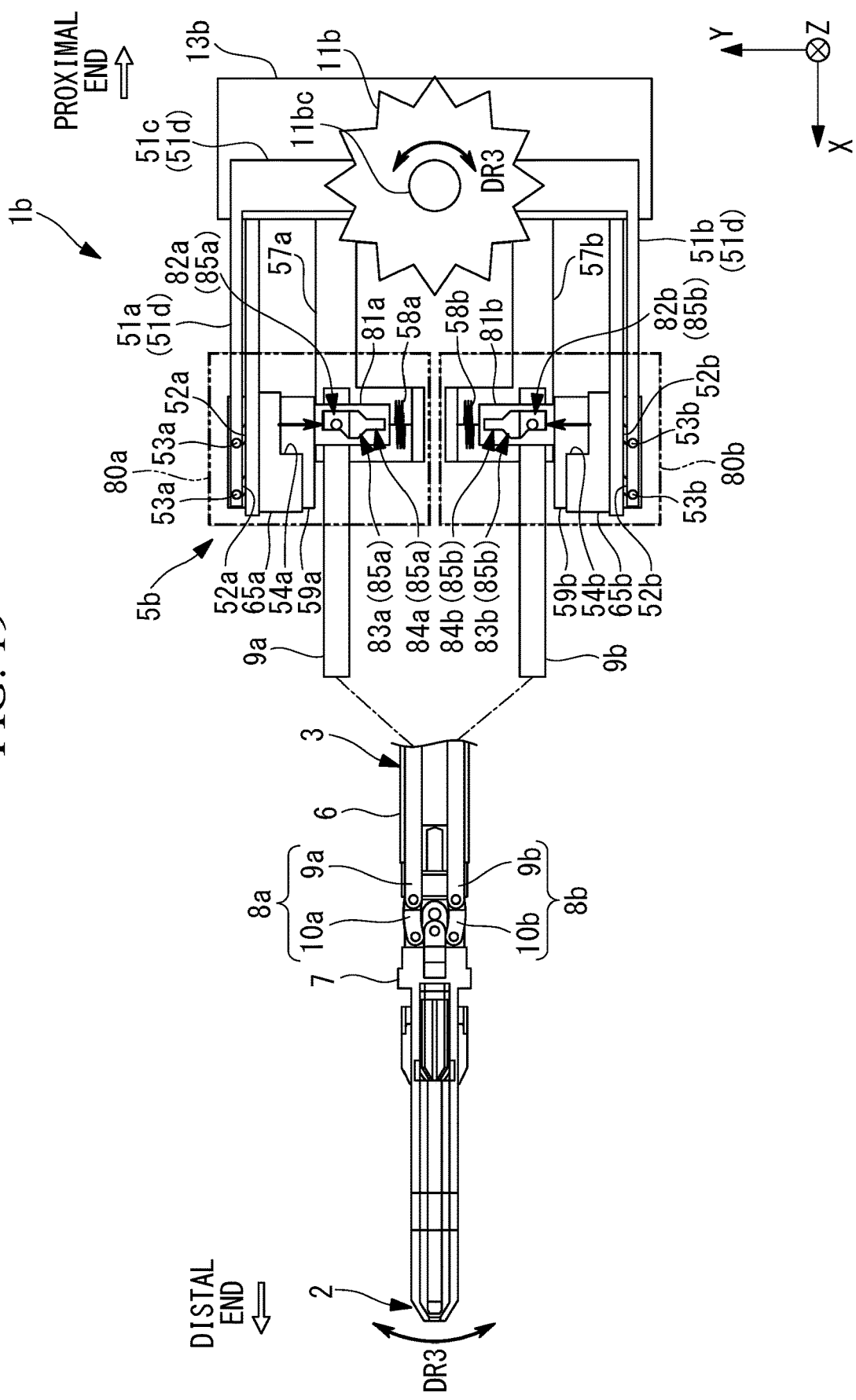
FIG. 19 is a sectional view showing the aforementioned portion of the medical manipulator of an exemplary embodiment, in a state in which the handle is pushed toward the distal end, thus allowing the bending mechanism to be bent.

FIG. 19 shows a state when a bending operation required for making the pivoting member 7 pivot by a large amount is performed. In this embodiment, as in the above embodiment shown in, for example, FIGS. 8-14B, in order to bend the pivoting member 7, it is necessary to move the handle 11b toward the distal end with respect to the base 13b. Compared with the state shown in FIG. 17, the handle 11b and the pushing member 51d shown in FIG. 19 are moved toward the distal end with respect to the base 13b. In this case, the surfaces of the groove cams 81a and 81b facing radially outward come into contact with the surfaces of the coma pushers 59a and 59b facing radially inward.

When the groove cams 81a and 81b are moved radially inward, the positions of the first links 9a and 9b along the Y-axis with respect to the guide grooves 85a and 85b of the groove cams 81a and 81b change. As shown in FIG. 19, the positions of the engagement parts 91a and 91b of the first links 9a and 9b along the Y-axis are located at the semi-fixing grooves 82a and 82b. The lengths of the semi-fixing grooves 82a and 82b along the X-axis are greater than the lengths of the fixing grooves 84a and 84b along the X-axis, so as to allow the first links 9a and 9b to be moved within the predetermined ranges along the X-axis. As in the above embodiment shown in, for example, FIGS. 8-14B, the reason for the difference in length therebetween is to absorb the difference in movement distance between the first links 9a and 9b and the second links 57a and 57b.

Figure 20:
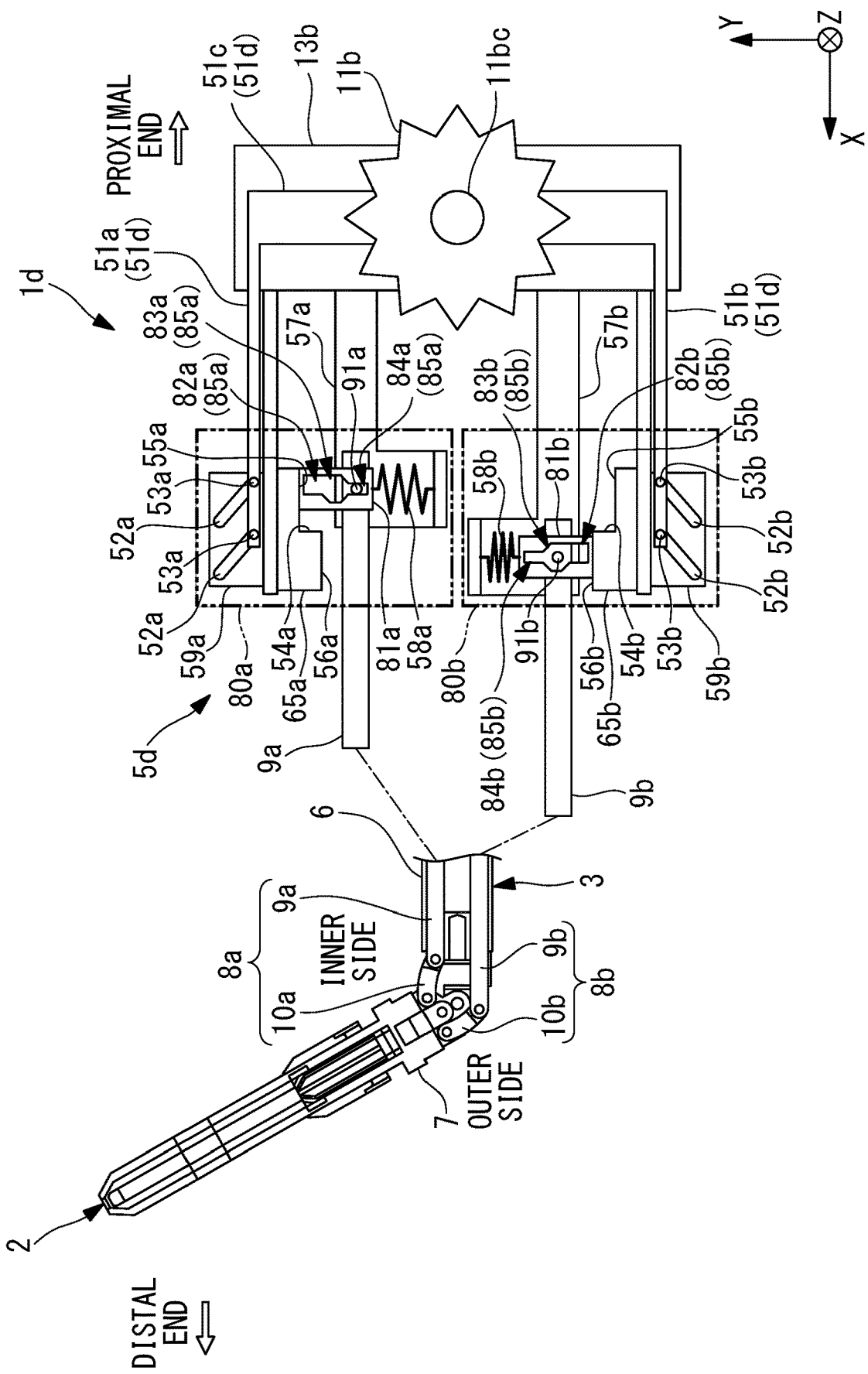
FIG. 20 is a sectional view showing the aforementioned portion of the medical manipulator of an exemplary embodiment, in a state in which the bending mechanism is bent.

In the state shown in FIG. 19, due to the biasing forces of the biasing members 58a and 58b, forces that push back the coma pushers 59a and 59b radially outward act. Accordingly, the handle 11b receives the force that pushes the handle 11b toward the proximal end. In this state, when the handle 11b and the pushing member 51d are operated so as to be gradually moved toward the proximal end, and the handle 11b is rotated, for example, clockwise, a state shown in FIG. 20 is obtained. Specifically, before the coma pusher 59b returns to the position at the radially outer side, which is shown in FIG. 17, the groove cam 81b is moved over the step surface 54b of the stopper member 65b and is moved to the position on the second surface 56b of the stopper member 65b. In contrast to this, the groove cam 81a is moved to the position on the first surface 55a of the stopper member 65a.

In this case, the first link 9a is engaged with the fixing groove 84a of the guide groove 85a, as in the state shown in FIG. 17. On the other hand, in the state shown in FIG. 20, the position of the engagement part 91b of the first link 9b along the Y-axis is located at a permissible groove 83b of the guide groove 85b. Thus, because the first link 9b does not come into contact with the groove cam 81b when moved along the X-axis, the first link 9b can be freely moved along the X-axis within a range in which the engagement pins 53b can be moved inside the slits 52b.

In the bending mechanism 5d and the medical manipulator 1d of this embodiment, which are thus configured, even if the handle 11b is rotated when the pivoting member 7 does not pivot, as shown in FIG. 17, the positions of the groove cams 81a and 81b along the X-axis are regulated by the step surfaces 54a and 54b of the stopper members 65a and 65b. Thus, the first links 9a and 9b can hardly be moved along the X-axis. From this state, when the handle 11b is pushed toward the distal end, as in the state shown in FIG. 19, the coma pushers 59a and 59b are moved radially inward, thereby moving the groove cams 81a and 81b radially inward. When the handle 11b is rotated from this state, the groove cams 81a and 81b can be moved within the predetermined ranges along the X-axis. Accordingly, the first links 9a and 9b can be moved along the X-axis, thus making it possible to make the pivoting member 7 pivot.

In the state shown in FIG. 20, in which the pivoting member 7 is bent, the permissible stress of the first link 9b, which is located at the outer side of the bending, is reduced more than the first link 9a, which is located at the inner side, as shown in the graph of FIG. 4. However, in the medical manipulator 1d of this embodiment, the position of the first link 9b, which is located at the outer side, along the X-axis is not regulated by the groove cam 81b. Thus, even when an external force is applied to the pivoting member 7, only the first link 9a, which is located at the inner side and the permissible stress of which is large, receives the external force, and the first link 9b, which is located at the outer side, need not receive the external force. Accordingly, it is possible to reduce damage to the first links 9a and 9b.

In the above-described embodiments, although a description has been given of, as examples, the bending mechanisms 5, 5a, 5b, 5c, and 5d and the medical manipulators 1, 1a, 1b, 1c, and 1d, which reduce, when the permissible stress of one of the two pairs of links 8a and 8b becomes less than the permissible stress of the other, an external force applied to the one, the permissible stress of which becomes less, it is possible to variously modify the bending mechanisms and the medical manipulators. For example, it is also possible to use known members for the first links 9a and 9b and the handles 11 and l1b, and to use another shape for the slits 22a and 22b, etc. formed in the intermediate members 21a and 21b.

The above-described embodiment also leads to the following aspects.

According to one aspect, the present disclosure relates to a bending mechanism including: an elongated support member; a pivoting member that is supported at a distal end of the support member so as to be pivotable about an axis intersecting a longitudinal axis of the support member; a first driving-force transmission member that is disposed along the longitudinal axis of the support member and that transmits a driving force applied at a proximal end, to make the pivoting member pivot with respect to the support member; a second driving-force transmission member that is disposed, along the longitudinal axis of the support member, at the opposite side of a central axis of the support member from the first driving-force transmission member, and that transmits a driving force applied at the proximal end, to make the pivoting member pivot with respect to the support member; and a coupling portion that is provided on at least one of the first driving-force transmission member and the second driving-force transmission member, and that switches a coupled state of the one so as to reduce a force to be transmitted to the one due to an external force applied to the pivoting member, when a permissible stress of the one becomes less than a permissible stress of the other.

According to this aspect, when a driving force is applied, at the proximal end of the support member, to the first driving-force transmission member and the second driving-force transmission member, the driving force transmitted by the first driving-force transmission member and the second driving-force transmission member is transmitted to the pivoting member, and the pivoting member is made to pivot about an axis, at the distal end of the support member. The permissible stress of the first driving-force transmission member and the permissible stress of the second driving-force transmission member will be different from each other depending on the pivoting direction of the pivoting member.

For example, if the permissible stress of the first driving-force transmission member, which is one of the driving-force transmission members, has become less than the permissible stress of the second driving-force transmission member, which is the other of the driving-force transmission members, the coupling portion provided on the first driving-force transmission member switches the coupled state so as to reduce the force to be transmitted by the first driving-force transmission member.

Accordingly, the second driving-force transmission member, the permissible stress of which has become relatively large due to bending, receives an external force applied to the pivoting member, and the first driving-force transmission member, the permissible stress of which has become less, need not receive an excessive stress, thereby making it possible to prevent damage to the first driving-force transmission member. In this case, because damage is prevented by changing the magnitude of the driving force to be transmitted, instead of increasing the rigidities of parts, including the first driving-force transmission member and the second driving-force transmission member, it is possible to achieve a reduction in the diameter of an insertion part by preventing an increase in the cross-section dimensions of parts.

In the above-described aspect, the coupling portion may switch the coupled state so as to reduce the force to be transmitted, when a pivoting angle of the pivoting member with respect to the support member exceeds a threshold.

By doing so, because the force to be transmitted is switched on the basis of the threshold, which is set in advance, it is possible to select, by setting the threshold, whether to receive an external force by one or both of the first driving-force transmission member and the second driving-force transmission member. Through this selection, the degree of freedom of the cross-section dimensions of parts and the diameter of the insertion part is increased.

The above-described aspect may further include an operating part that makes the pivoting member pivot with respect to the support member, by the pivoting angle determined in accordance with an operation amount, wherein the coupling portion may switch the coupled state so as to reduce the force to be transmitted, when the pivoting angle exceeds the threshold.

By doing so, the threshold used for switching the magnitude of a driving force to be transferred is associated with the operation amount received by the operating part. Through this association, the threshold for a pivoting angle to be determined in accordance with the operation amount is set.

In the above-described aspect, the coupling portion may include a groove cam that has a guide groove, and an engagement part that is engaged with the guide groove of the groove cam in the longitudinal-axis direction; and an engagement position in the longitudinal-axis direction between the guide groove and the engagement part may be switched in accordance with the operation amount.

By doing so, an area where the coupling portion can be freely moved along the longitudinal-axis direction is produced depending on the engagement position of the engagement part in the longitudinal-axis direction. In the state in which the coupling portion can be freely moved, an excessive stress need not be received, thus making it possible to prevent damage to the first driving-force transmission member or the second driving-force transmission member, which has the coupling portion.

In the above-described aspect, the guide groove may include a restricting area where the position of the engagement part in the longitudinal-axis direction with respect to the guide groove is fixed, and a free-movement area where the position of the engagement part in the longitudinal-axis direction with respect to the guide groove is freely movable; and the position of the engagement part in the longitudinal-axis direction may be switched from the restricting area to the free-movement area when the pivoting angle exceeds the threshold.

By doing so, when the position of the engagement part is switched to be in the free-movement area, on the basis of the threshold, which is set in accordance with the pivoting angle, the first driving-force transmission member or the second driving-force transmission member, which has the coupling portion, need not receive an excessive stress.

In the above-described aspect, the coupling portion may be provided on each of the first driving-force transmission member and the second driving-force transmission member, the guide groove may further include a semi-restricting area where movement of the engagement part in the longitudinal-axis direction with respect to the guide groove is restricted within a predetermined range, and the bending mechanism may further include a mechanism that disposes the engagement parts in the semi-restricting areas when a pivoting operation of the pivoting member is performed and that disposes, in the free-movement area, one of the engagement parts that is located closer to the distal end, in the longitudinal-axis direction, than the other one of the engagement parts is and disposes the other one of the engagement parts in the restricting area, when the pivoting operation is not performed in a state in which the pivoting member has pivoted.

By doing so, because the engagement parts in the coupling portions are allowed to move within the predetermined ranges by being disposed in the semi-restricting areas, even when the first driving-force transmission member and the second driving-force transmission member are operated by the same operation amount by using the operating part, it is possible to make the pivoting member pivot so as not to apply an unreasonable force to the first driving-force transmission member and the second driving-force transmission member.

In the above-described aspect, the mechanism may switch, in response that the operating part undergoes a release operation, from a regulated state in which pivoting of the pivoting member is regulated to a pivotable state in which the pivoting member is pivotable, and may dispose the engagement parts in the semi-restricting areas.

By doing so, in a state in which the release operation is not accepted, the pivoting member is not bent, and, in a state in which the release operation is accepted, the pivoting member is bent in accordance with the operation amount. Accordingly, even when the first driving-force transmission member and the second driving-force transmission member are operated by the same operation amount by using the operating part, it is possible to make the pivoting member pivot so as not to apply an unreasonable force to the first driving-force transmission member and the second driving-force transmission member.

In the above-described aspect, at least one of the first driving-force transmission member and the second driving-force transmission member, which has the coupling portion, may include: a distal-end transmission member that is connected to a distal end of the coupling portion and that is moved in the longitudinal-axis direction; and a proximal-end transmission member that is connected to a proximal end of the coupling portion and that is moved in the longitudinal-axis direction; the coupling portion may include: a bellcrank that is fixed to the proximal-end transmission member so as to be pivotable about a pivoting center; and a groove cam that has a guide groove; one end of the bellcrank may be fixed to a proximal end of the distal-end transmission member; and, when the pivoting angle exceeds the threshold, the other end of the bellcrank may be switched to a pivotable state from a state in which the position of the bellcrank in a direction perpendicular to the longitudinal-axis direction with respect to the guide groove is fixed.

By doing so, with a small number of parts, mainly including the bellcrank, it is possible that the first driving-force transmission member or the second driving-force transmission member, the permissible stress of which has become less, need not receive an excessive stress.

In the above-described aspect, the coupling portion may allow the first driving-force transmission member and the second driving-force transmission member to transmit the driving force in both directions of the longitudinal axis of the support member.

By doing so, when the driving force is transmitted in both directions of the longitudinal axis of the support member, the occurrence of an excessive stress can be prevented in any of the directions.

Furthermore, according to another aspect, the present disclosure relates to a medical manipulator including: the bending mechanism according to the above-described aspect; and a treatment tool that is attached to the pivoting member.

According to this aspect, the first driving-force transmission member and the second driving-force transmission member need not receive an excessive stress, thus making it possible to reduce damage to the first driving-force transmission member and the second driving-force transmission member.

REFERENCE SIGNS LIST 1, 1a, 1b, 1c, 1d medical manipulator
2 treatment tool
4 operating part
5, 5a, 5b, 5c, 5d bending mechanism
support member
pivoting member
9a first link (first driving-force transmission member, distal-end transmission member)
9b first link (second driving-force transmission member, distal-end transmission member)
14a, 15a, 57a second link (first driving-force transmission member, proximal-end transmission member)
14b, 15b, 57b second link (second driving-force transmission member, proximal-end transmission member)
30a, 30b, 40a, 40b, 50a, 50b, 70a, 70b, 80a, 80b coupling portion
58a, 58b biasing member
31a, 31b, 49a, 49b, 71a, 71b, 81a, 81b groove cam
60a, 60b coma (groove cam)
37a, 37b, 46a, 46b, 74a, 74b small-width groove (restricting area)
63a, 63b, 84a, 84b fixing groove (restricting area)
35a, 35b, 48a, 48b, 72a, 72b large-width groove (free-movement area)
61a, 61b, 82a, 82b semi-fixing groove (semi-restricting area)
62a, 62b, 83a, 83b permissible groove (free-movement area)
91a, 91b engagement part
93a, 93b small-width section (engagement part)
41a, 41b bellcrank
44a, 44b pivoting central axis (pivoting center)

The invention claimed is:

1. A bending mechanism comprising:
an elongated support member extending along a longitudinal axis;
a swivel that is pivotably connected to a distal end of the support member so as to be pivotable about an axis intersecting the longitudinal axis of the support member;
a handle configured to be operated to pivot the swivel with respect to the support member by a pivoting angle determined in accordance with an amount of operation on the handle;
a first link and a second link disposed opposite to the first link along the longitudinal axis of the support member, the first and second links each being coupled at a respective proximal end to the handle and being configured to transmit a driving force received from the handle to pivot the swivel with respect to the support member; and
a connector that is provided on at least one of the first and second links, and includes a groove cam that has a guide groove, an engagement part of the at least one of the first and second links being engaged with the guide groove of the groove cam in a direction of the longitudinal axis, an engagement position between the guide groove and the engagement part being configured to be moved in the direction of the longitudinal axis in accordance with the amount of operation on the handle,
wherein the connector is configured to switch one of the first and second links from a first coupled state to a second coupled state when the pivoting angle of the swivel exceeds a threshold such that a permissible stress of the one of the first and second links becomes less than a permissible stress of the other of the first and second links.

2. The bending mechanism according to claim 1, wherein:
the guide groove comprises:
a first groove portion having a first width in the direction of the longitudinal axis such that when the engagement part is positioned in the first groove portion, the engagement part is fixed with respect to the guide groove in the direction of the longitudinal axis, and
a second groove portion having a second width in the direction of the longitudinal axis that is larger than the first width such that the engagement part is movable in the direction of the longitudinal axis with respect to the guide groove when the engagement part is positioned in the second groove portion; and
in the first coupled state, the engagement part is in the first groove portion, and in the second coupled state, the engagement part is in the second groove portion.

3. The bending mechanism according to claim 2, wherein:
the connector is provided on each of the first link and the second link such that the connector is coupled to engagement parts of the first and second links,
the guide groove further comprises a third groove portion sized such that when the engagement part is in the third groove portion, movement of the engagement part with respect to the guide groove in the direction of the longitudinal axis is restricted within a predetermined range, and
the bending mechanism is configured to:
dispose the engagement parts in the third groove portion during a pivoting operation of the swivel, and
dispose one of the engagement parts in the second groove portion, and the other of the engagement parts in the first groove portion such that the one of the engagement parts is positioned distal of the other of the engagement parts in the direction of the longitudinal axis in a state in which the swivel has pivoted.

4. The bending mechanism according to claim 3, wherein the bending mechanism is configured to switch from a regulated state in which pivoting of the swivel is regulated to a pivotable state in which the swivel is pivotable and the engagement parts are disposed in the third groove portion in response to the handle undergoing a release operation.

5. The bending mechanism according to claim 1, wherein:
at least one of the first and second links, on which the connector is provided, comprises:
a distal-end transmission member that is connected to a distal end of the connector and that is configured to move in the direction of the longitudinal axis; and
a proximal-end transmission member that is connected to a proximal end of the connector and that is configured to move in the direction of the longitudinal axis;
the connector comprises:

a bellcrank that is fixed to the proximal-end transmission member so as to be pivotable about a pivoting center; and a groove cam that has a guide groove;

one end of the bellcrank is fixed to a proximal end of the distal-end transmission member; and when the pivoting angle exceeds the threshold, the other end of the bellcrank is configured to switch to a pivotable state from a fixed state in which the position of the bellcrank is fixed with respect to the guide groove in a direction perpendicular to the longitudinal axis.

6. The bending mechanism according to claim 1, wherein the connector allows the first link and the second link to transmit the driving force in both directions of the longitudinal axis of the support member.

7. The bending mechanism according to claim 1, wherein the bending mechanism is configured to reduce an external force transmitted to one of the first and second links when in the second coupled state.

8. The bending mechanism according to claim 1, wherein:

the connector is configured to switch the one of the first and second links that is located on an outer side with respect to the pivoting of the swivel between the first coupled state and the second coupled state;

in the first coupled state, the engagement part is not movable in the direction of the longitudinal axis with respect to the guide groove; and in the second coupled state, the engagement part is movable in the direction of the longitudinal axis with respect to the guide groove.

9. The bending mechanism according to claim 8, wherein the other of the first and second links is located on an inner side with respect to the pivoting of the swivel.

10. A medical manipulator comprising:

the bending mechanism according to claim 1; and a treatment tool that is attached to the swivel.

11. A bending mechanism comprising:

an elongated support member extending along a longitudinal axis;

a swivel that is pivotably connected to a distal end of the support member so as to be pivotable about an axis intersecting the longitudinal axis of the support member;

a handle configured to be operated to pivot the swivel with respect to the support member by a pivoting angle determined in accordance with an amount of operation on the handle;

a first link and a second link disposed opposite to the first link along the longitudinal axis of the support member, the first and second links each being coupled at a respective proximal end to the handle and being configured to linearly move in the direction of the longitudinal axis to pivot the swivel with respect to the support member; and a connector including:

a first connector that is provided on the first link, and includes a first groove cam that has a first guide groove, a first engagement part of the first link being engaged with the first guide groove of the first groove cam in a direction of the longitudinal axis; and a second connector that is provided on the second link, and includes a second groove cam that has a second guide groove, a second engagement part of the second link being engaged with the second guide groove of the second groove cam in a direction of the longitudinal axis;

wherein:

a first engagement position between the first guide groove and the first engagement part and a second engagement position between the second guide groove and the second engagement part are configured to be moved along the longitudinal axis in accordance with the amount of operation on the handle;

the connector is configured to switch one of the first and second links that is located on an outer side with respect to the pivoting of the swivel from a first coupled state to a second coupled state when the pivoting angle of the swivel exceeds a threshold;

in the first coupled state, the one of the first and second engagement parts is not movable in the direction of the longitudinal axis with respect to the one of the first and second guide grooves; and in the second coupled state, the one of the first and second engagement parts is movable in the direction of the longitudinal axis with respect to the one of the first and second guide grooves.

* * * * *